(12) United States Patent
Raab et al.

(10) Patent No.: US 8,945,853 B2
(45) Date of Patent: Feb. 3, 2015

(54) DETECTION OF INTRACELLULAR BINDING EVENTS BY MEASURING PROTEIN ABUNDANCE

(71) Applicant: DiscoveRx Corporation, Fremont, CA (US)

(72) Inventors: William Raab, San Francisco, CA (US); Thomas S. Wehrman, Mountain View, CA (US)

(73) Assignee: DiscoveRx Corporation, Fremont, CA (US)

(*) Notice: Subject to any disclaimer, the term of this patent is extended or adjusted under 35 U.S.C. 154(b) by 0 days.

(21) Appl. No.: 13/759,691

(22) Filed: Feb. 5, 2013

(65) Prior Publication Data
US 2013/0203067 A1 Aug. 8, 2013

Related U.S. Application Data

(60) Provisional application No. 61/595,525, filed on Feb. 6, 2012.

(51) Int. Cl.
*G01N 33/53* (2006.01)
*G01N 33/569* (2006.01)
*G01N 33/50* (2006.01)

(52) U.S. Cl.
CPC ...... *G01N 33/56966* (2013.01); *G01N 33/5008* (2013.01)
USPC .......................................................... 435/7.1

(58) Field of Classification Search
None
See application file for complete search history.

(56) References Cited

U.S. PATENT DOCUMENTS

| | | | |
|---|---|---|---|
| 4,378,428 | A | 3/1983 | Farina et al. |
| 5,444,161 | A | 8/1995 | Manning et al. |
| 5,643,734 | A | 7/1997 | Henderson |
| 5,935,840 | A | 8/1999 | Anderson et al. |
| 7,220,552 | B1 | 5/2007 | Crabtree et al. |
| 7,479,377 | B2 | 1/2009 | Zhao et al. |
| 2004/0137480 | A1 | 7/2004 | Eglen |
| 2005/0136488 | A1 | 6/2005 | Horecka et al. |
| 2005/0287522 | A1 | 12/2005 | Blau et al. |
| 2007/0275397 | A1 | 11/2007 | Wehrman et al. |
| 2008/0306127 | A9 | 12/2008 | Castro et al. |
| 2009/0098588 | A1 | 4/2009 | Wehrman et al. |
| 2010/0034777 | A1 | 2/2010 | Wandless et al. |
| 2010/0120063 | A1 | 5/2010 | Bassoni et al. |
| 2010/0203555 | A1 | 8/2010 | Wehrman et al. |
| 2010/0285451 | A1 | 11/2010 | Blau et al. |
| 2012/0077204 | A1 | 3/2012 | Blau et al. |
| 2012/0329075 | A1 | 12/2012 | Wehrman et al. |

FOREIGN PATENT DOCUMENTS

| | | |
|---|---|---|
| EP | 2487183 A1 | 8/2012 |
| WO | 86/02666 A1 | 5/1986 |
| WO | 00/71702 A1 | 11/2000 |
| WO | 01/94617 A2 | 12/2001 |

OTHER PUBLICATIONS

Langley et al., "Molecular Basis of Beta-Galactosidase alpha-Complementation", Proc. Nat. Acad. Sci. USA, vol. 72, No. 4, pp. 1254-1257, Apr. 1975.
International Search Report and Written Opinion, PCT/US13/24789, mailed Apr. 23, 2013.
Foit,et al., "Optimizing Protein Stability in Vivo", Molecular Cell, 36, 861-871, Dec. 11, 2009.
Lampson et al., "Targeting Protein Stability with a Small Molecule", Cell 126, Sep. 8, 2006, pp. 827-829.
Yewdell, et al., "Out with the old, in with the new? Comparing methods for measuring protein degradation", Cell Biol. Int., 2011, vol. 35, 6 pages.
Kim, et al., "Stepwise Activation of BAX and BAK by tBID, BIM and PUMA Initiates Mitochondrial Apoptosis", Molecular Cell 36, 487-499, Nov. 13, 2009.
Zacharias, et al., "Molecular Biology and Mutation of Green Fluorescent Protein", Green Fluorescent Protein: Properties, Applications, and Protocols, Second Edition, Copyright 2006, pp. 83-118.
Szegezdi, et al., "Bcl-2 family on guard at the ER", Am J Physiol Cell Physiol 296: C941-C953, 2009.
Kirkpatrick, et al., "GPS navigation of the protein-stability landscape", Nature Biotechnology, vol. 27, No. 1, Jan. 2009, pp. 46-48.
Henderson, et al., "CEDIA, a New Homogeneous Immunoassay System", Clinical Chemistry, vol. 32, No. 9, 1986, pp. 1637-1641.
Wehrman, et al., "Enzymatic detection of protein translocation", Nature Methods, vol. 2, No. 7, Jul. 2005, pp. 521-527.
Mohler, et al., "Gene expression and cell fusion analyzed by lacZ complementation in mammalian cells", Proc. Natl. Acad. Sci. USA, vol. 93, Oct. 1996, pp. 12423-12427.
Yan, et al., "Cell-Based High-Throughput Screening Assay System for Monitoring G Protein-Coupled Receptor Activation Using Beta-Galactosidase Enzyme Complementation Technology", Journal of Biomolecular Screening, vol. 7, No. 5, 2002, pp. 451-459/.
Eglen, et al., "Beta Galactosidase Enzyme Fragment Complementation as a Novel Technology for High Throughput Screening", Combinatorial Chemistry & High Throughput Screening, vol. 6, No. 4, 2003, pp. 381-387.
Eglen, "Enzyme Fragment Complementation: A Flexible High Throughput Screening ASSAY Technology", ASSAY and Drug Development Technologies, vol. 1, No. 1-1, 2002, pp. 97-104.
Wehrman, et al., "Protein-protein interactions monitored in mammalian cells via complementation of beta-lactamase enzyme fragments", PNAS, vol. 99, No. 6, Mar. 19, 2002, pp. 3469-3474.

(Continued)

*Primary Examiner* — Suzanne M Noakes
(74) *Attorney, Agent, or Firm* — David J. Aston; Peters Verny, LLP

(57) ABSTRACT

Methods and compositions are provided to measure the binding of a test compound to a target peptide by measuring the effect of the compound on the abundance of the target peptide inside a cell. The target peptide may bind the test compound at an active site or an allosteric site, and it has been found that such binding may stabilize the target peptide against cellular degradation. The target peptide will preferably comprise a destabilizing mutation which shortens the half life of the target peptide within the cell, typically a mammalian cell. Test compounds, including small molecules, have been found to stabilize target peptides. Also provided are systems and kits for use in practicing the methods.

21 Claims, 10 Drawing Sheets

SEQUENCE LISTING

<160> NUMBER OF SEQ ID NOS: 20

<210> SEQ ID NO 1
<211> LENGTH: 52
<212> TYPE: PRT
<213> ORGANISM: Escherichia coli

<400> SEQUENCE: 1

Met Gly Val Ile Thr Asp Ser Leu Ala Val Val Leu Gln Arg Arg Asp
1               5                   10                  15

Trp Glu Asn Pro Gly Val Thr Gln Leu Asn Arg Leu Ala Ala His Pro
            20                  25                  30

Pro Phe Ala Ser Trp Arg Asn Ser Glu Glu Ala Arg Thr Asp Arg Pro
        35                  40                  45

Ser Gln Gln Leu
    50

<210> SEQ ID NO 2
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asn Ser Leu Ala Val Val Leu Gln Arg Arg Asp Trp Glu Asn Pro Gly
1               5                   10                  15

Val Thr Gln Leu Asn Arg Leu Ala Ala His Pro Pro Phe Ala Ser Trp
            20                  25                  30

Arg Asn Ser Glu Glu Ala Arg Thr Asp Arg
        35                  40

<210> SEQ ID NO 3
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Gly Val Ile Thr Asp Ser Leu Ala Val Val Leu Gln Arg Arg Asp
1               5                   10                  15

Trp Glu Asn Pro Gly Val Thr Gln Leu Asn Arg Leu Ala Ala His Pro
            20                  25                  30

Pro Phe Ala Ser Tyr Arg Asn Ser Glu Glu Ala Arg Thr Asp Arg Pro
        35                  40                  45

Ser Gln Gln Leu
    50

<210> SEQ ID NO 4
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asn Ser Leu Ala Val Val Leu Gln Arg Arg Asp Trp Glu Asn Pro Gly
1               5                   10                  15

```
Val Thr Gln Leu Asn Arg Leu Ala Ala His Pro Pro Phe Ala Ser Trp
             20                  25                  30

Arg Asn Ser Glu Glu Ala Arg Thr Asp Arg
             35                  40

<210> SEQ ID NO 5
<211> LENGTH: 991
<212> TYPE: PRT
<213> ORGANISM: Escherichia coli

<400> SEQUENCE: 5

Met Gly Val Ile Thr Asp Ser Leu Ala Val Ala Arg Thr Asp Arg
 1               5                  10                  15

Pro Ser Gln Gln Leu Arg Ser Leu Asn Gly Glu Trp Arg Phe Ala Trp
             20                  25                  30

Phe Pro Ala Pro Glu Ala Val Pro Glu Ser Trp Leu Glu Cys Asp Leu
             35                  40                  45

Pro Glu Ala Asp Thr Val Val Pro Ser Asn Trp Gln Met His Gly
         50                  55                  60

Tyr Asp Ala Pro Ile Tyr Thr Asn Val Thr Tyr Pro Ile Thr Val Asn
 65                  70                  75                  80

Pro Pro Phe Val Pro Thr Glu Asn Pro Thr Gly Cys Tyr Ser Leu Thr
             85                  90                  95

Phe Asn Val Asp Glu Ser Trp Leu Gln Glu Gly Gln Thr Arg Ile Ile
            100                 105                 110

Phe Asp Gly Val Asn Ser Ala Phe His Leu Trp Cys Asn Gly Arg Trp
            115                 120                 125

Val Gly Tyr Gly Gln Asp Ser Arg Leu Pro Ser Glu Phe Asp Leu Ser
            130                 135                 140

Ala Phe Leu Arg Ala Gly Glu Asn Arg Leu Ala Val Met Val Leu Arg
145                 150                 155                 160

Trp Ser Asp Gly Ser Tyr Leu Glu Asp Gln Asp Met Trp Arg Met Ser
                165                 170                 175

Gly Ile Phe Arg Asp Val Ser Leu Leu His Lys Pro Thr Thr Gln Ile
            180                 185                 190

Ser Asp Phe His Val Ala Thr Arg Phe Asn Asp Asp Phe Ser Arg Ala
            195                 200                 205

Val Leu Glu Ala Glu Val Gln Met Cys Gly Glu Leu Arg Asp Tyr Leu
            210                 215                 220

Arg Val Thr Val Ser Leu Trp Gln Gly Glu Thr Gln Val Ala Ser Gly
225                 230                 235                 240

Thr Ala Pro Phe Gly Gly Glu Ile Ile Asp Glu Arg Gly Gly Tyr Ala
                245                 250                 255

Asp Arg Val Thr Leu Arg Leu Asn Val Glu Asn Pro Lys Leu Trp Ser
            260                 265                 270

Ala Glu Ile Pro Asn Leu Tyr Arg Ala Val Val Glu Leu His Thr Ala
            275                 280                 285

Asp Gly Thr Leu Ile Glu Ala Glu Cys Asp Val Gly Phe Arg Glu Val
            290                 295                 300

Arg Ile Glu Asn Gly Leu Leu Leu Leu Asn Gly Lys Pro Leu Leu Ile
305                 310                 315                 320

Arg Gly Val Asn Arg His Glu His His Pro Leu His Gly Gln Val Met
                325                 330                 335

Asp Glu Gln Thr Met Val Gln Asp Ile Leu Leu Met Lys Gln Asn Asn
            340                 345                 350
```

```
Phe Asn Ala Val Arg Cys Ser His Tyr Pro Asn His Pro Leu Trp Tyr
            355                 360                 365

Thr Leu Cys Asp Arg Tyr Gly Leu Tyr Val Val Asp Glu Ala Asn Ile
    370                 375                 380

Glu Thr His Gly Met Val Pro Met Asn Arg Leu Thr Asp Asp Pro Arg
385                 390                 395                 400

Trp Leu Pro Ala Met Ser Glu Arg Val Thr Arg Met Val Gln Arg Asp
                405                 410                 415

Arg Asn His Pro Ser Val Ile Ile Trp Ser Leu Gly Asn Glu Ser Gly
            420                 425                 430

His Gly Ala Asn His Asp Ala Leu Tyr Arg Trp Ile Lys Ser Val Asp
        435                 440                 445

Pro Ser Arg Pro Val Gln Tyr Glu Gly Gly Ala Asp Thr Thr Ala
    450                 455                 460

Thr Asp Ile Ile Cys Pro Met Tyr Ala Arg Val Asp Glu Asp Gln Pro
465                 470                 475                 480

Phe Pro Ala Val Pro Lys Trp Ser Ile Lys Lys Trp Leu Ser Leu Pro
                485                 490                 495

Gly Glu Thr Arg Pro Leu Ile Leu Cys Glu Tyr Ala His Ala Met Gly
            500                 505                 510

Asn Ser Leu Gly Gly Phe Ala Lys Tyr Trp Gln Ala Phe Arg Gln Tyr
        515                 520                 525

Pro Arg Leu Gln Gly Gly Phe Val Trp Asp Trp Val Asp Gln Ser Leu
    530                 535                 540

Ile Lys Tyr Asp Glu Asn Asn Pro Trp Ser Ala Tyr Gly Gly Asp Phe
545                 550                 555                 560

Gly Asp Thr Pro Asn Asp Arg Gln Phe Cys Met Asn Gly Leu Val Phe
                565                 570                 575

Ala Asp Arg Thr Pro His Pro Ala Leu Thr Glu Ala Lys His Gln Gln
            580                 585                 590

Gln Phe Phe Gln Phe Arg Leu Ser Gly Gln Thr Ile Glu Val Thr Ser
        595                 600                 605

Glu Tyr Leu Phe Arg His Ser Asp Asn Glu Leu Leu His Trp Met Val
    610                 615                 620

Ala Leu Asp Gly Lys Pro Leu Ala Ser Gly Glu Val Pro Leu Asp Val
625                 630                 635                 640

Ala Pro Gln Gly Lys Gln Leu Ile Glu Leu Pro Glu Leu Pro Gln Pro
                645                 650                 655

Glu Ser Ala Gly Gln Leu Trp Leu Thr Val Arg Val Val Gln Pro Asn
            660                 665                 670

Ala Thr Ala Trp Ser Glu Ala Gly His Ile Ser Ala Trp Gln Gln Trp
        675                 680                 685

Arg Leu Ala Glu Asn Leu Ser Val Thr Leu Pro Ala Ala Ser His Ala
    690                 695                 700

Ile Pro His Leu Thr Thr Ser Glu Met Asp Phe Cys Ile Glu Leu Gly
705                 710                 715                 720

Asn Lys Arg Trp Gln Phe Asn Arg Gln Ser Gly Phe Leu Ser Gln Met
                725                 730                 735

Trp Ile Gly Asp Lys Lys Gln Leu Leu Thr Pro Leu Arg Asp Gln Phe
            740                 745                 750

Thr Arg Ala Pro Leu Asp Asn Asp Ile Gly Val Ser Glu Ala Thr Arg
    755                 760                 765
```

```
Ile Asp Pro Asn Ala Trp Val Glu Arg Trp Lys Ala Ala Gly His Tyr
770                 775                 780
Gln Ala Glu Ala Ala Leu Leu Gln Cys Thr Ala Asp Thr Leu Ala Asp
785                 790                 795                 800
Ala Val Leu Ile Thr Thr Ala His Ala Trp Gln His Gln Gly Lys Thr
                805                 810                 815
Leu Phe Ile Ser Arg Lys Thr Tyr Arg Ile Asp Gly Ser Gly Gln Met
            820                 825                 830
Ala Ile Thr Val Asp Val Glu Val Ala Ser Asp Thr Pro His Pro Ala
        835                 840                 845
Arg Ile Gly Leu Asn Cys Gln Leu Ala Gln Val Ala Glu Arg Val Asn
850                 855                 860
Trp Leu Gly Leu Gly Pro Gln Glu Asn Tyr Pro Asp Arg Leu Thr Ala
865                 870                 875                 880
Ala Cys Phe Asp Arg Trp Asp Leu Pro Leu Ser Asp Met Tyr Thr Pro
                885                 890                 895
Tyr Val Phe Pro Ser Glu Asn Gly Leu Arg Cys Gly Thr Arg Glu Leu
            900                 905                 910
Asn Tyr Gly Pro His Gln Trp Arg Gly Asp Phe Gln Phe Asn Ile Ser
        915                 920                 925
Arg Tyr Ser Gln Gln Gln Leu Met Glu Thr Ser His Arg His Leu Leu
930                 935                 940
His Ala Glu Glu Gly Thr Trp Leu Asn Ile Asp Gly Phe His Met Gly
945                 950                 955                 960
Ile Gly Gly Asp Asp Ser Trp Ser Pro Ser Val Ser Ala Glu Phe Gln
                965                 970                 975
Leu Ser Ala Gly Arg Tyr His Tyr Gln Leu Val Trp Cys Gln Lys
            980                 985                 990
```

<210> SEQ ID NO 6
<211> LENGTH: 4187
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6

```
tagttattaa tagtaatcaa ttacggggtc attagttcat agcccatata tggagttccg    60
cgttacataa cttacggtaa atggcccgcc tggctgaccg cccaacgacc cccgcccatt   120
gacgtcaata atgacgtatg ttcccatagt aacgccaata gggactttcc attgacgtca   180
atgggtggag tatttacggt aaactgccca cttggcagta catcaagtgt atcatatgcc   240
aagtacgccc cctattgacg tcaatgacgg taaatggccc gcctggcatt atgcccagta   300
catgacctta tgggactttc ctacttggca gtacatctac gtattagtca tcgctattac   360
catggtgatg cggttttggc agtacatcaa tgggcgtgga tagcggtttg actcacgggg   420
atttccaagt ctccacccca ttgacgtcaa tgggagtttg ttttggcacc aaaatcaacg   480
ggactttcca aaatgtcgta acaactccgc cccattgacg caaatgggcg gtaggcgtgt   540
acggtggag tctatataa gcagagctgg tttagtgaac cgtcagatcc gctagcgcta   600
ccggactcag atctcgagct caagcttcga attctgcagt cgacggtacc gcgggcccgg   660
gatccaccgg ccgtcgcca ccatgagctc caattcactg gccgtcgttt acaacgtcg   720
tgactgggaa aaccctggcg ttacccaact taatcgcctt gcagcacatc cccctttcgc   780
```

-continued

```
cagctggcgt aatagcgaag aggcccgcac cgatcgccct cccaacagtt gcgcagcct     840 gaatggcgaa taggcggccg cgactctaga tcataatcag ccataccaca tttgtagagg    900
ttttacttgc tttaaaaaac ctcccacacc tcccctgaa cctgaaacat aaaatgaatg    960
caattgttgt tgttaacttg tttattgcag cttataatgg ttacaaataa agcaatagca   1020
tcacaaattt cacaaataaa gcattttttt cactgcattc tagttgtggt ttgtccaaac   1080
tcatcaatgt atcttaaggc gtaaattgta agcgttaata ttttgttaaa attgcgttaa   1140 aattttttgtt aaatcagctc atttttttaac caataggccg aaatcggcaa aatcccttat  1200
aaatcaaaag aatagaccga datagggttg agtgttgttc cagtttggaa caagagtcca   1260
ctattaaaga acgtggactc caacgtcaaa gggcgaaaaa ccgtctatca gggcgatggc   1320
ccactacgtg aaccatcacc ctaatcaagt tttttggggt cgaggtgccg taaagcacta   1380
aatcggaacc ctaaagggag cccccgattt agagcttgac ggggaaagcc ggcgaacgtg   1440
gcgagaaagg aagggaagaa agcgaaagga gcgggcgcta gggcgctggc aagtgtagcg   1500
gtcacgctgc gcgtaaccac cacacccgcc gcgcttaatg cgccgctaca gggcgcgtca   1560
ggtggcactt ttcggggaaa tgtgcgcgga acccctattt gtttatttttt ctaaatacat   1620 tcaaatatgt atccgctcat gagacaataa ccctgataaa tgcttcaata atattgaaaa   1680
aggaagagtc ctgaggcgga aagaaccagc tgtggaatgt gtgtcagtta gggtgtggaa   1740
agtccccagg ctccccagca ggcagaagta tgcaaagcat gcatctcaat tagtcagcaa   1800
ccaggtgtgg aaagtcccca ggctccccag caggcagaag tatgcaaagc atgcatctca   1860
attagtcagc aaccatagtc ccgcccctaa ctccgcccat cccgccccta actccgccca   1920
gttccgccca ttctccgccc catggctgac taattttttt tatttatgca gaggccgagg   1980
ccgcctcggc ctctgagcta ttccagaagt agtgaggagg ctttttttgga ggcctaggct   2040 tttgcaaaga tcgatcaaga dacaggatga ggatcgtttc gcatgattga caagatgga   2100 ttgcacgcag gttctccggc cgcttgggtg gagaggctat tcggctatga ctgggcacaa   2160
cagacaatcg gctgctctga tgccgccgtg ttccggctgt cagcgcaggg gcgcccggtt   2220 cttttttgtca agaccgacct gtccggtgcc ctgaatgaac tgcaagacga ggcagcgcgg   2280
ctatcgtggc tggccacgac gggcgttcct tgcgcagctg tgctcgacgt tgtcactgaa   2340
gcgggaaggg actggctgct attgggcgaa gtgccggggc aggatctcct gtcatctcac   2400
cttgctcctg ccgagaaagt atccatcatg gctgatgcaa tgcggcggct gcatacgctt   2460
gatccggcta cctgcccatt cgaccaccaa gcgaaacatc gcatcgagcg agcacgtact   2520
cggatggaag ccggtcttgt cgatcaggat gatctggacg aagagcatca ggggctcgcg   2580
ccagccgaac tgttcgccag gctcaaggcg agcatgcccg acggcgagga tctcgtcgtg   2640
acccatggcg atgcctgctt gccgaatatc atggtggaaa atggccgctt ttctggattc   2700
atcgactgtg gccggctggg tgtggcggac cgctatcagg acatagcgtt ggctacccgt   2760
gatattgctg aagagcttgg cggcgaatgg gctgaccgct tcctcgtgct ttacggtatc   2820
gccgctcccg attcgcagcg catcgccttc tatcgccttc ttgacgagtt cttctgagcg   2880
ggactctggg gttcgaaatg accgaccaag cgacgcccaa cctgccatca cgagatttcg   2940
attccaccgc cgccttctat gaaaggttgg gcttcggaat cgttttccgg gacgccggct   3000
ggatgatcct ccagcgcggg gatctcatgc tggagttctt cgcccaccct aggggggaggc   3060 taactgaaac acggaaggag acaataccgg aaggaacccg cgctatgacg gcaataaaaa   3120
gacagaataa aacgcacggt gttgggtcgt ttgttcataa acgcggggtt cggtcccagg   3180
```

```
gctggcactc tgtcgatacc ccaccgagac cccattgggg ccaatacgcc cgcgtttctt    3240
ccttttcccc accccacccc ccaagttcgg gtgaaggccc agggctcgca gccaacgtcg    3300
gggcggcagg ccctgccata gcctcaggtt actcatatat actttagatt gatttaaaac    3360
ttcattttta atttaaaagg atctaggtga agatcctttt tgataatctc atgaccaaaa    3420
tcccttaacg tgagttttcg ttccactgag cgtcagaccc cgtagaaaag atcaaaggat    3480
cttcttgaga tcctttttt ctgcgcgtaa tctgctgctt gcaaacaaaa aaaccaccgc    3540
taccagcggt ggtttgtttg ccggatcaag agctaccaac tcttttttccg aaggtaactg    3600 gcttcagcag agcgcagata ccaaatactg tccttctagt gtagccgtag ttaggccacc    3660
acttcaagaa ctctgtagca ccgcctacat acctcgctct gctaatcctg ttaccagtgg    3720
ctgctgccag tggcgataag tcgtgtctta ccgggttgga ctcaagacga tagttaccgg    3780
ataaggcgca gcggtcgggc tgaacggggg gttcgtgcac acagcccagc ttggagcgaa    3840
cgacctacac cgaactgaga tacctacagc gtgagctatg agaaagcgcc acgcttcccg    3900
aagggagaaa ggcggacagg tatccggtaa gcggcagggt cggaacagga gagcgcacga    3960
gggagcttcc agggggaaac gcctggtatc tttatagtcc tgtcgggttt cgccacctct    4020
gacttgagcg tcgatttttg tgatgctcgt caggggggcg gagcctatgg aaaaacgcca    4080
gcaacgcggc ctttttacgg ttcctggcct tttgctggcc ttttgctcac atgttctttc    4140
ctgcgttatc ccctgattct gtggataacc gtattaccgc catgcat              4187
```

<210> SEQ ID NO 7
<211> LENGTH: 302
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

```
Met Leu Arg Leu Val Arg Lys Leu Gly Ser Gly Gln Phe Gly Glu Val
1               5                   10                  15

Trp Met Gly Tyr Tyr Lys Asn Asn Met Lys Val Ala Ile Lys Thr Leu
            20                  25                  30

Lys Glu Gly Thr Met Ser Pro Glu Ala Phe Leu Gly Glu Ala Asn Val
        35                  40                  45

Met Lys Ala Leu Gln His Glu Arg Leu Val Arg Leu Tyr Ala Val Val
    50                  55                  60

Thr Lys Glu Pro Ile Tyr Ile Val Thr Glu Tyr Met Ala Arg Gly Cys
65                  70                  75                  80

Leu Leu Asp Phe Leu Lys Thr Asp Glu Gly Ser Arg Leu Ser Leu Pro
                85                  90                  95

Arg Leu Ile Asp Met Ser Ala Gln Ile Ala Glu Gly Met Ala Tyr Ile
            100                 105                 110

Glu Arg Met Asn Ser Ile His Arg Asp Leu Arg Ala Ala Asn Ile Leu
        115                 120                 125

Val Ser Glu Ala Leu Cys Cys Lys Ile Ala Asp Phe Gly Leu Ala Arg
    130                 135                 140

Ile Ile Asp Ser Glu Tyr Thr Ala Gln Glu Gly Ala Lys Phe Pro Ile
145                 150                 155                 160

Lys Trp Thr Ala Pro Glu Ala Ile His Phe Gly Val Phe Thr Ile Lys
                165                 170                 175
```

```
Ala Asp Val Trp Ser Phe Gly Val Leu Met Glu Val Val Thr Tyr
            180                 185                 190
Gly Arg Val Pro Tyr Pro Gly Met Ser Asn Pro Glu Val Ile Arg Asn
        195                 200                 205
Leu Glu Arg Gly Tyr Arg Met Pro Arg Pro Asp Thr Cys Pro Pro Glu
    210                 215                 220
Leu Tyr Arg Gly Val Ile Ala Glu Cys Trp Arg Ser Arg Pro Glu Glu
225                 230                 235                 240
Arg Pro Thr Phe Glu Phe Leu Gln Ser Val Leu Ser Ser Phe Glu Leu
                245                 250                 255
Leu Glu Ser Ser Asn Ser Leu Ala Val Val Leu Gln Arg Arg Asp Trp
            260                 265                 270
Glu Asn Pro Gly Val Thr Gln Leu Asn Arg Leu Ala Ala His Pro Pro
        275                 280                 285
Phe Ala Ser Trp Arg Asn Ser Glu Glu Ala Arg Thr Asp Arg
    290                 295                 300

<210> SEQ ID NO 8
<211> LENGTH: 20
<212> TYPE: PRT
<213> ORGANISM: Unknown
<220> FEATURE:
<223> OTHER INFORMATION: Description of Unknown: Truncated BIM peptide

<400> SEQUENCE: 8

Met Arg Pro Glu Ile Trp Ile Ala Gln Glu Leu Arg Arg Ile Gly Asp
1               5                   10                  15
Glu Phe Asn Ala
            20

<210> SEQ ID NO 9
<211> LENGTH: 16
<212> TYPE: PRT
<213> ORGANISM: Unknown
<220> FEATURE:
<223> OTHER INFORMATION: Description of Unknown: Truncated BAK peptide

<400> SEQUENCE: 9

Gly Gln Val Gly Arg Gln Leu Ala Ile Ile Gly Asp Asp Ile Asn Arg
1               5                   10                  15

<210> SEQ ID NO 10
<211> LENGTH: 21
<212> TYPE: PRT
<213> ORGANISM: Unknown
<220> FEATURE:
<223> OTHER INFORMATION: Description of Unknown: Truncated BAX peptide

<400> SEQUENCE: 10

Gln Asp Ala Ser Thr Lys Lys Leu Ser Glu Cys Leu Lys Arg Ile Gly
1               5                   10                  15
Asp Glu Leu Asp Ser
            20

<210> SEQ ID NO 11
<211> LENGTH: 71
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11
```

-continued

```
Met Arg Pro Glu Ile Trp Ile Ala Gln Glu Leu Arg Arg Ile Gly Asp
1               5                   10                  15

Glu Phe Asn Ala Ser Ser Phe Glu Leu Leu Glu Ser Ser Asn Ser Leu
            20                  25                  30

Ala Val Val Leu Gln Arg Arg Asp Trp Glu Asn Pro Gly Val Thr Gln
                35                  40                  45

Leu Asn Arg Leu Ala Ala His Pro Pro Phe Ala Ser Trp Arg Asn Ser
        50                  55                  60

Glu Glu Ala Arg Thr Asp Arg
65                  70

<210> SEQ ID NO 12
<211> LENGTH: 366
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Gln Lys Val Gly Glu Leu Lys Asp Asp Phe Glu Lys Ile Ser
1               5                   10                  15

Glu Leu Gly Ala Gly Asn Gly Gly Val Val Phe Lys Val Ser His Lys
            20                  25                  30

Pro Ser Gly Leu Val Met Ala Arg Lys Leu Ile His Leu Glu Ile Lys
                35                  40                  45

Pro Ala Ile Arg Asn Gln Ile Ile Arg Glu Leu Gln Val Leu His Glu
        50                  55                  60

Cys Asn Ser Pro Tyr Ile Val Gly Phe Tyr Gly Ala Phe Tyr Ser Asp
65                  70                  75                  80

Gly Glu Ile Ser Ile Cys Met Glu His Met Asp Gly Gly Ser Leu Asp
                85                  90                  95

Gln Val Leu Lys Lys Ala Gly Arg Ile Pro Glu Gln Ile Leu Gly Lys
            100                 105                 110

Val Ser Ile Ala Val Ile Lys Gly Leu Thr Tyr Leu Arg Glu Lys His
                115                 120                 125

Lys Ile Met His Arg Asp Val Lys Pro Ser Asn Ile Leu Val Asn Ser
        130                 135                 140

Arg Gly Glu Ile Lys Leu Cys Asp Phe Gly Val Ser Gly Gln Leu Ile
145                 150                 155                 160

Asp Ser Met Ala Asn Ser Phe Val Gly Thr Arg Ser Tyr Met Ser Pro
                165                 170                 175

Glu Arg Leu Gln Gly Thr His Tyr Ser Val Gln Ser Asp Ile Trp Ser
            180                 185                 190

Met Gly Leu Ser Leu Val Glu Met Ala Val Gly Arg Tyr Pro Ile Pro
        195                 200                 205

Pro Pro Asp Ala Lys Glu Leu Glu Leu Met Phe Gly Cys Gln Val Glu
    210                 215                 220

Gly Asp Ala Ala Glu Thr Pro Pro Arg Pro Arg Thr Pro Gly Arg Pro
225                 230                 235                 240

Leu Ser Ser Tyr Gly Met Asp Ser Arg Pro Pro Met Ala Ile Phe Glu
                245                 250                 255

Leu Leu Asp Tyr Ile Val Asn Glu Pro Pro Pro Lys Leu Pro Ser Gly
            260                 265                 270

Val Phe Ser Leu Glu Phe Gln Asp Phe Val Asn Lys Cys Leu Ile Lys
```

```
                275                 280                 285

Asn Pro Ala Glu Arg Ala Asp Leu Lys Gln Leu Met Val His Ala Phe
            290                 295                 300

Ile Lys Arg Ser Asp Ala Glu Glu Val Asp Phe Ser Ser Phe Glu Leu
305                 310                 315                 320

Leu Glu Ser Ser Asn Ser Leu Ala Val Val Leu Gln Arg Arg Asp Trp
                325                 330                 335

Glu Asn Pro Gly Val Thr Gln Leu Asn Arg Leu Ala Ala His Pro Pro
            340                 345                 350

Phe Ala Ser Trp Arg Asn Ser Glu Glu Ala Arg Thr Asp Arg
                355                 360                 365

<210> SEQ ID NO 13
<211> LENGTH: 162
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Lys Val Ser Glu Gln Leu Lys Cys Cys Ser Gly Ile Leu Lys Glu
1               5                   10                  15

Met Phe Ala Lys Lys His Ala Ala Tyr Ala Trp Pro Phe Tyr Lys Pro
            20                  25                  30

Val Asp Val Glu Ala Leu Gly Leu His Asp Tyr Cys Asp Ile Ile Lys
        35                  40                  45

His Pro Met Asp Met Ser Thr Ile Lys Ser Lys Leu Glu Ala Arg Glu
    50                  55                  60

Tyr Arg Asp Ala Gln Glu Phe Gly Ala Asp Val Arg Leu Met Phe Ser
65                  70                  75                  80

Asn Cys Tyr Lys Tyr Asn Pro Pro Asp His Glu Val Val Ala Met Ala
                85                  90                  95

Arg Lys Leu Gln Asp Val Phe Glu Met Arg Phe Ala Lys Met Pro Ser
            100                 105                 110

Ser Phe Glu Leu Leu Glu Ser Ser Asn Ser Leu Ala Val Val Leu Gln
        115                 120                 125

Arg Arg Asp Trp Glu Asn Pro Gly Val Thr Gln Leu Asn Arg Leu Ala
    130                 135                 140

Ala His Pro Pro Phe Ala Ser Trp Arg Asn Ser Glu Glu Ala Arg Thr
145                 150                 155                 160

Asp Arg

<210> SEQ ID NO 14
<211> LENGTH: 167
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Arg Val Thr Asn Gln Leu Gln Tyr Leu His Lys Val Met Lys
1               5                   10                  15

Ala Leu Trp Lys His Gln Phe Ala Trp Pro Phe Arg Gln Pro Val Asp
            20                  25                  30

Ala Val Lys Leu Gly Leu Pro Asp Tyr His Lys Ile Ile Lys Gln Pro
        35                  40                  45
```

```
Met Asp Met Gly Thr Ile Lys Arg Arg Leu Glu Asn Tyr Tyr Trp
        50                  55                  60

Ala Ala Ser Glu Cys Met Gln Asp Phe Asn Thr Met Phe Thr Asn Cys
65                  70                  75                  80

Tyr Ile Tyr Asn Lys Pro Thr Asp Asp Ile Val Leu Met Ala Gln Thr
                    85                  90                  95

Leu Glu Lys Ile Phe Leu Gln Lys Val Ala Ser Met Pro Gln Glu Glu
                100                 105                 110

Gln Glu Leu Val Ser Ser Phe Glu Leu Leu Glu Ser Ser Asn Ser Leu
            115                 120                 125

Ala Val Val Leu Gln Arg Arg Asp Trp Glu Asn Pro Gly Val Thr Gln
        130                 135                 140

Leu Asn Arg Leu Ala Ala His Pro Pro Phe Ala Ser Trp Arg Asn Ser
145                 150                 155                 160

Glu Glu Ala Arg Thr Asp Arg
                165

<210> SEQ ID NO 15
<211> LENGTH: 155
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Leu Thr Asn Gln Leu Gln Tyr Leu Gln Lys Val Val Leu Lys Asp
1               5                   10                  15

Leu Trp Lys His Ser Phe Ser Trp Pro Phe Gln Arg Pro Val Asp Ala
                20                  25                  30

Val Lys Leu Gln Leu Pro Asp Tyr Tyr Thr Ile Ile Lys Asn Pro Met
            35                  40                  45

Asp Leu Asn Thr Ile Lys Lys Arg Leu Glu Asn Lys Tyr Tyr Ala Lys
        50                  55                  60

Ala Ser Glu Cys Ile Glu Asp Phe Asn Thr Met Phe Ser Asn Cys Tyr
65                  70                  75                  80

Leu Tyr Asn Lys Pro Gly Asp Asp Ile Val Leu Met Ala Gln Ala Leu
                85                  90                  95

Glu Lys Leu Phe Met Gln Lys Leu Ser Ser Phe Glu Leu Leu Glu Ser
                100                 105                 110

Ser Asn Ser Leu Ala Val Val Leu Gln Arg Arg Asp Trp Glu Asn Pro
            115                 120                 125

Gly Val Thr Gln Leu Asn Arg Leu Ala Ala His Pro Pro Phe Ala Ser
        130                 135                 140

Trp Arg Asn Ser Glu Glu Ala Arg Thr Asp Arg
145                 150                 155

<210> SEQ ID NO 16
<211> LENGTH: 458
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Ser Thr Ala Thr Thr Val Ala Pro Ala Gly Ile Pro Ala Thr Pro
1               5                   10                  15
```

-continued

Gly Pro Val Asn Pro Pro Pro Glu Val Ser Asn Pro Ser Lys Pro
            20                  25                  30

Gly Arg Lys Thr Asn Gln Leu Gln Tyr Met Gln Asn Val Val Lys
            35                  40                  45

Thr Leu Trp Lys His Gln Phe Ala Trp Pro Phe Tyr Gln Pro Val Asp
 50                  55                  60

Ala Ile Lys Leu Asn Leu Pro Asp Tyr His Lys Ile Ile Lys Asn Pro
 65                  70                  75                  80

Met Asp Met Gly Thr Ile Lys Lys Arg Leu Glu Asn Asn Tyr Tyr Trp
                85                  90                  95

Ser Ala Ser Glu Cys Met Gln Asp Phe Asn Thr Met Phe Thr Asn Cys
            100                 105                 110

Tyr Ile Tyr Asn Lys Pro Thr Asp Asp Ile Val Leu Met Ala Gln Ala
            115                 120                 125

Leu Glu Lys Ile Phe Leu Gln Lys Val Ala Gln Met Pro Gln Glu Glu
 130                 135                 140

Val Glu Leu Leu Pro Pro Ala Pro Lys Gly Lys Gly Arg Lys Pro Ala
145                 150                 155                 160

Ala Gly Ala Gln Ser Ala Gly Thr Gln Gln Val Ala Ala Val Ser Ser
            165                 170                 175

Val Ser Pro Ala Thr Pro Phe Gln Ser Val Pro Pro Thr Val Ser Gln
            180                 185                 190

Thr Pro Val Ile Ala Ala Thr Pro Val Pro Thr Ile Thr Ala Asn Val
            195                 200                 205

Thr Ser Val Pro Val Pro Pro Ala Ala Pro Pro Pro Ala Thr
            210                 215                 220

Pro Ile Val Pro Val Val Pro Thr Pro Val Val Lys Lys Lys
225                 230                 235                 240

Gly Val Lys Arg Lys Ala Asp Thr Thr Thr Pro Thr Thr Ser Ala Ile
            245                 250                 255

Thr Ala Ser Arg Ser Glu Ser Pro Pro Pro Leu Ser Asp Pro Lys Gln
            260                 265                 270

Ala Lys Val Val Ala Arg Arg Glu Ser Gly Arg Pro Ile Lys Pro
            275                 280                 285

Pro Lys Lys Asp Leu Glu Asp Gly Glu Val Pro Gln His Ala Gly Lys
 290                 295                 300

Lys Gly Lys Leu Ser Glu His Leu Arg Tyr Cys Asp Ser Ile Leu Arg
305                 310                 315                 320

Glu Met Leu Ser Lys Lys His Ala Ala Tyr Ala Trp Pro Phe Tyr Lys
            325                 330                 335

Pro Val Asp Ala Glu Ala Leu Glu Leu His Asp Tyr His Asp Ile Ile
            340                 345                 350

Lys His Pro Met Asp Leu Ser Thr Val Lys Arg Lys Met Asp Gly Arg
            355                 360                 365

Glu Tyr Pro Asp Ala Gln Gly Phe Ala Ala Asp Val Arg Leu Met Phe
            370                 375                 380

Ser Asn Cys Tyr Lys Tyr Asn Pro Pro Asp His Glu Val Val Ala Met
385                 390                 395                 400

Ala Arg Lys Ser Asn Cys Cys Ile Ser Phe Glu Leu Leu Glu Ser Ser
            405                 410                 415

Asn Ser Leu Ala Val Val Leu Gln Arg Arg Asp Trp Glu Asn Pro Gly
            420                 425                 430

Val Thr Gln Leu Asn Arg Leu Ala Ala His Pro Pro Phe Ala Ser Trp
         435                 440                 445

Arg Asn Ser Glu Glu Ala Arg Thr Asp Arg
         450                 455

<210> SEQ ID NO 17
<211> LENGTH: 328
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Thr Glu Lys Ile Ile Cys Arg Asp Val Ala Arg Gly Tyr Glu Asn
1               5                   10                  15

Val Pro Ile Pro Cys Val Asn Gly Val Asp Gly Glu Pro Cys Pro Glu
            20                  25                  30

Asp Tyr Lys Tyr Ile Ser Glu Asn Cys Glu Thr Ser Thr Met Asn Ile
        35                  40                  45

Asp Arg Asn Ile Thr His Leu Gln His Cys Thr Cys Val Asp Asp Cys
    50                  55                  60

Ser Ser Ser Asn Cys Leu Cys Gly Gln Leu Ser Ile Arg Cys Trp Tyr
65                  70                  75                  80

Asp Lys Asp Gly Arg Leu Leu Gln Glu Phe Asn Lys Ile Glu Pro Pro
                85                  90                  95

Leu Ile Phe Glu Cys Asn Gln Ala Cys Ser Cys Trp Arg Asn Cys Lys
            100                 105                 110

Asn Arg Val Val Gln Ser Gly Ile Lys Val Arg Leu Gln Leu Tyr Arg
        115                 120                 125

Thr Ala Lys Met Gly Trp Gly Val Arg Ala Leu Gln Thr Ile Pro Gln
    130                 135                 140

Gly Thr Phe Ile Cys Glu Tyr Val Gly Glu Leu Ile Ser Asp Ala Glu
145                 150                 155                 160

Ala Asp Val Arg Glu Asp Asp Ser Tyr Leu Phe Asp Leu Asp Asn Lys
                165                 170                 175

Asp Gly Glu Val Tyr Cys Ile Asp Ala Arg Tyr Tyr Gly Asn Ile Ser
            180                 185                 190

Arg Phe Ile Asn His Leu Cys Asp Pro Asn Ile Ile Pro Val Arg Val
        195                 200                 205

Phe Met Leu His Gln Asp Leu Arg Phe Pro Arg Ile Ala Phe Phe Ser
    210                 215                 220

Ser Arg Asp Ile Arg Thr Gly Glu Glu Leu Gly Phe Asp Tyr Gly Asp
225                 230                 235                 240

Arg Phe Trp Asp Ile Lys Ser Lys Tyr Phe Thr Cys Gln Cys Gly Ser
                245                 250                 255

Glu Lys Cys Lys His Ser Ala Glu Ala Ile Ala Leu Gly Gln Ser Arg
            260                 265                 270

Leu Ala Arg Leu Asp Leu Ser Phe Glu Leu Leu Glu Ser Ser Asn Ser
        275                 280                 285

Leu Ala Val Val Leu Gln Arg Arg Asp Trp Asn Pro Gly Val Thr
    290                 295                 300

Gln Leu Asn Arg Leu Ala Ala His Pro Pro Phe Ala Ser Trp Arg Asn
305                 310                 315                 320

Ser Glu Glu Ala Arg Thr Asp Arg
                325

```
<210> SEQ ID NO 18
<211> LENGTH: 559
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Trp Glu Leu Val Ala Leu Leu Leu Thr Leu Ala Tyr Leu Phe
1               5                   10                  15

Trp Pro Lys Arg Arg Cys Pro Gly Ala Lys Tyr Pro Lys Ser Leu Leu
                20                  25                  30

Ser Leu Pro Leu Val Gly Ser Leu Pro Phe Leu Pro Arg His Gly His
            35                  40                  45

Met His Asn Asn Phe Phe Lys Leu Gln Lys Lys Tyr Gly Pro Ile Tyr
        50                  55                  60

Ser Val Arg Met Gly Thr Lys Thr Thr Val Ile Val Gly His His Gln
65                  70                  75                  80

Leu Ala Lys Glu Val Leu Ile Lys Lys Gly Lys Asp Phe Ser Gly Arg
                85                  90                  95

Pro Gln Met Ala Thr Leu Asp Ile Ala Ser Asn Asn Arg Lys Gly Ile
                100                 105                 110

Ala Phe Ala Asp Ser Gly Ala His Trp Gln Leu His Arg Arg Leu Ala
            115                 120                 125

Met Ala Thr Phe Ala Leu Phe Lys Asp Gly Asp Gln Lys Leu Glu Lys
        130                 135                 140

Ile Ile Cys Gln Glu Ile Ser Thr Leu Cys Asp Met Leu Ala Thr His
145                 150                 155                 160

Asn Gly Gln Ser Ile Asp Ile Ser Phe Pro Val Phe Val Ala Val Thr
                165                 170                 175

Asn Val Ile Ser Leu Ile Cys Phe Asn Thr Ser Tyr Lys Asn Gly Asp
            180                 185                 190

Pro Glu Leu Asn Val Ile Gln Asn Tyr Asn Glu Gly Ile Ile Asp Asn
        195                 200                 205

Leu Ser Lys Asp Ser Leu Val Asp Leu Val Pro Trp Leu Lys Ile Phe
    210                 215                 220

Pro Asn Lys Thr Leu Glu Lys Leu Lys Ser His Val Lys Ile Arg Asn
225                 230                 235                 240

Asp Leu Leu Asn Lys Ile Leu Glu Asn Tyr Lys Glu Lys Phe Arg Ser
                245                 250                 255

Asp Ser Ile Thr Asn Met Leu Asp Thr Leu Met Gln Ala Lys Met Asn
            260                 265                 270

Ser Asp Asn Gly Asn Ala Gly Pro Asp Gln Asp Ser Glu Leu Leu Ser
        275                 280                 285

Asp Asn His Ile Leu Thr Thr Ile Gly Asp Ile Phe Gly Ala Gly Val
    290                 295                 300

Glu Thr Thr Thr Ser Val Val Lys Trp Thr Leu Ala Phe Leu Leu His
305                 310                 315                 320

Asn Pro Gln Val Lys Lys Lys Leu Tyr Glu Glu Ile Asp Gln Asn Val
                325                 330                 335

Gly Phe Ser Arg Thr Pro Thr Ile Ser Asp Arg Asn Arg Leu Leu Leu
            340                 345                 350

Leu Glu Ala Thr Ile Arg Glu Val Leu Arg Leu Arg Pro Val Ala Pro
```

```
                    355                 360                 365
Met Leu Ile Pro His Lys Ala Asn Val Asp Ser Ser Ile Gly Glu Phe
    370                 375                 380

Ala Val Asp Lys Gly Thr Glu Val Ile Ile Asn Leu Trp Ala Leu His
385                 390                 395                 400

His Asn Glu Lys Glu Trp His Gln Pro Asp Gln Phe Met Pro Glu Arg
                405                 410                 415

Phe Leu Asn Pro Ala Gly Thr Gln Leu Ile Ser Pro Ser Val Ser Tyr
                420                 425                 430

Leu Pro Phe Gly Ala Gly Pro Arg Ser Cys Ile Gly Glu Ile Leu Ala
                435                 440                 445

Arg Gln Glu Leu Phe Leu Ile Met Ala Trp Leu Leu Gln Arg Phe Asp
            450                 455                 460

Leu Glu Val Pro Asp Asp Gly Gln Leu Pro Ser Leu Glu Gly Ile Pro
465                 470                 475                 480

Lys Val Val Phe Leu Ile Asp Ser Phe Lys Val Lys Ile Lys Val Arg
                485                 490                 495

Gln Ala Trp Arg Glu Ala Gln Ala Glu Gly Ser Thr Ser Ser Phe Glu
                500                 505                 510

Leu Leu Glu Ser Ser Asn Ser Leu Ala Val Val Leu Gln Arg Arg Asp
            515                 520                 525

Trp Glu Asn Pro Gly Val Thr Gln Leu Asn Arg Leu Ala Ala His Pro
            530                 535                 540

Pro Phe Ala Ser Trp Arg Asn Ser Glu Glu Ala Arg Thr Asp Arg
545                 550                 555

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 19

His His His His His His
1               5

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      polyhistidine tag
<220> FEATURE:
<221> NAME/KEY: misc_feature
<222> LOCATION: (1)..(10)
<223> OTHER INFORMATION: This sequence may encompass 5-10 residues

<400> SEQUENCE: 20

His His His His His His His His His His
1               5                   10
```

DETECTION OF INTRACELLULAR BINDING EVENTS BY MEASURING PROTEIN ABUNDANCE

CROSS-REFERENCE TO RELATED APPLICATIONS

This application claims priority from U.S. Provisional Patent Application No. 61/595,525, filed Feb. 6, 2012, which is hereby incorporated by reference in its entirety.

STATEMENT OF GOVERNMENTAL SUPPORT

None.

REFERENCE TO SEQUENCE LISTING, COMPUTER PROGRAM, OR COMPACT DISK

In accordance with "Legal Framework for EFS-Web," (2006 Apr. 11) Applicants submit herewith a sequence listing as an ASCII text file. The text file will serve as both the paper copy required by 37 CFR 1.821(c) and the computer readable form (CRF) required by 37 CFR 1.821(e). The date of creation of the file was Jan. 31, 2013, is named 3817411.txt, and the size of the ASCII text file in bytes is 41,160. Applicants incorporate the contents of the sequence listing by reference in its entirety.

BACKGROUND OF THE INVENTION

1. Field of the Invention

The present invention relates generally to methods which monitor binding of a compound to a target of interest inside a mammalian cell by increasing the stability of the target of interest and therefore its abundance, or number of molecules, in a cell. Further, the invention also relates to screening small molecules as inhibitors of target-compound binding in a cell.

2. Related Art

Presented below is background information on certain aspects of the present invention as they may relate to technical features referred to in the detailed description, but not necessarily described in detail. That is, individual parts or methods used in the present invention may be described in greater detail in the materials discussed below, which materials may provide further guidance to those skilled in the art for making or using certain aspects of the present invention as claimed. The discussion below should not be construed as an admission as to the relevance of the information to any claims herein or the prior art effect of the material described.

Binding between and among various molecules such as proteins is central to biological processes essential for normal cell functioning. Cellular pathways, such as signal transduction, apoptosis, cell and growth proliferation, gene regulation, require a series of interactions and bindings between and among specific proteins. Following transcription and translation, proteins assume their functional shape or confirmation through synchronized protein folding. The correct protein folding is essential for proteins to carry out their desired functions and expression. Proteins which do not undergo folding or do not fold in the requisite manner will have a short half-life in a cell and will be discarded by the cell as the degradation system of the cell will recognize it as an improper protein. Properly folded proteins will have a longer half-life and participate in binding events or other required cellular functions. Thus, stability of proteins is essential for protein expression and functioning in a cell, which is achieved through correct structure and participating in binding events leading to complex formation.

Protein binding occurs through special characteristic sequences or surfaces which are known as interacting interfaces. E.g. in case of protein-protein interactions these interfaces are known as 'hotspots' and constitute tight fitting regions which are generally characterized by complementary pockets scattered through the central region of the interface and enriched in structurally conserved residues (Hubbard and Argos Cavities and packing at protein interfaces. Protein Sci 1994; 3: 2194-2206). These pockets are classified as "complementary" (Binkowski et al, Inferring functional relationships of proteins from local sequence and spatial surface patterns J. Mol Biol 2003; 332: 505-526) because there is a large complementarity both in shape and in the juxtaposition of hydrophobic and hydrophilic hot spots, with buried charged residues (Arkin and Wells Small molecule inhibitors of protein-protein interactions: progressing towards the dream. Nat Rev Drug Discov 2004; 3: 301-317). The "hotspots" are the essential amino acid sequences to participate in binding and to carry out physiological functions.

Other aspect of protein function is the allosteric modulation and has long been recognized as a general and widespread mechanism for the control of protein function. Modulators bind to regulatory sites distinct from the active site (hotspots) on the protein, resulting in conformational changes that may profoundly influence protein function and is a classical control mechanism of protein behavior. As described above, proteins are in native state as they undergo allosteric modulation.

Of particular importance (and exemplified below) are protein kinases, which participate in the process of phosphorylation, whereby they transfer phosphate groups from high-energy donor molecules, such as ATP to specific substrates. Protein phosphorylation is one of the most significant signal transduction mechanisms by which intercellular signals regulate crucial intracellular processes such as ion transport, cellular proliferation, and hormone responses. Kinases are the key regulators of cell function that constitute one of the largest and most functionally diverse gene families. They direct the activity, localization and overall function of many proteins and almost all cellular processes. Protein kinases can be regulated by activator proteins, inhibitor proteins, ligand binding to regulatory subunits, cofactors and phosphorylation by other proteins or by themselves (autophosphorylation). Kinases are prominent in signal transduction and co-ordination of complex functions such as the cell cycle. Thus, it makes kinases a potential target class for therapeutic interventions in many disease states such as cancer, diabetes, inflammation, and arthritis and represent as much as thirty percent of all protein targets under investigation by pharmaceutical companies.

A number of methods have been developed and used to study cellular binding events. Physical methods such as protein affinity chromatography, affinity blotting, immunoprecipitation and cross-linking however, either detect interactions that are so weak or else detect nearest neighbors which may not be in direct contact. Library-based methods such as protein probing and phage display also have certain intrinsic limitations. Two-hybrid system is only limited to proteins that can be localized to the nucleus, which may prevent its use with certain extracellular proteins. Translocation assays are very time consuming and expensive, as they require a confocal fluorescence system and are plagued by artifacts such as intrinsic fluorescence from combinatorial libraries and background fluorescence. However, none of the method is easy to perform, can be done in high throughput mode are amenable to studying disruption of constitutive biological complexes and identifying interaction interface.

Further, systems for protein stabilization and destabilization assays have also been developed. Studies by Stankunas et al (Stankunas K., Bayle H., Havranek J J., Wandless T J., Baker D., Crabtree G R., Gestwicki J E. Rescue of degradation-prone mutants of the FK506-Rapamycin binding (FRB) protein with chemical ligands; ChemBioChem, 2007; 8(10): 1162-1169) have shown the rescue of degradation prone mutants of FRB protein with chemical ligands. However, owing to the structure and half-life of luciferase in a cell it may interfere with the functioning of the target protein and also limits the availability of ligands to stabilize the fusion protein for the binding assays.

Earlier studies and assays have focused on large peptides and natural products as the primary compound classes capable of modulating cellular bindings. However a growing number of evidence has suggested that small molecules also modulate the interactions responsible for biological complexes (Toogood, Inhibition of protein-protein association by small molecules: approaches and progress. J Med Chem 2002, 45:1543-1558. Berg T, Modulation of protein-protein interactions with small organic molecules. Angew Chem Int Ed Engl 2003, 42:2462-2481). There are a number of advantages in using small molecules as inhibitors owing to higher metabolic stability, bioavailability, easier synthesis and great solubility among others.

The present invention is exemplified by use of enzyme fragment complementation. First shown in prokaryotes, enzyme fragment complementation (EFC) using beta-galactosidase (β-gal) is based on the complementation of enzyme fragments to form an active enzyme See, e.g., Ullman et al., *J. Mol. Biol.* 24:339-43 (1967); Ullman et al., *J. Mol. Biol.* 32:1-13 (1968); Ullman et al., *J. Mol. Biol.* 12:918-23 (1965). These systems have important advantages including low level expression of the test proteins, generation of signal as a direct result of the interaction, and enzymatic amplification. As a result, they are highly sensitive and physiologically relevant assays. See, e.g., Blakely et al., *Nat. Biotechnol.* 18:218-22 (2000).

SPECIFIC PATENTS AND PUBLICATIONS

Wandless et al. US 2010/0034777, published Feb. 11, 2010, entitled "Method for Regulating Protein Function in Cells In Vivo Using Synthetic Small Molecules," discloses a system for conditionally controlling protein stability. A genetic fusion of a destabilizing domain (DD) to a protein of interest (POI) results in degradation of the entire fusion protein. Exemplified destabilizing domains are derived from FKBP, and the stabilizing ligand is Shield 1.

US Patent Application US2005/0136488 "Cellular Membrane Protein Assay," published Jun. 23, 2005 and owned by the present assignee discloses various β-galactosidase enzyme donor or "ED" sequences for use in β-galactosidase enzyme fragment complementation.

US Patent Application US2005/0287522 "Detection of Protein Translocation by beta-galactosidase Reporter Fragment Complementation," published Dec. 29, 2005, discloses various methodologies for monitoring protein translocation using enzyme fragment complementation.

U.S. Pat. No. 7,479,377, entitled "Genetic Construct Intracellular Monitoring System", dated Jan. 20, 2009 and owned by the present assignee discloses system to monitor intracellular events using fusion protein which employ using genetic construct for introduction of fusion protein into a cell.

BRIEF SUMMARY OF THE INVENTION

The following brief summary is not intended to include all features and aspects of the present invention, nor does it imply that the invention must include all features and aspects discussed in this summary.

The present invention concerns an assay whereby a target peptide to be assayed is fused to a labeling peptide and expressed as a fusion protein in a eukaryotic cell, preferably a mammalian cell. As the target peptide binds a test compound it forms a complex and is stabilized, thus changing the amount of fusion protein in a cell, i.e. the abundance of the fusion protein (and the target peptide component thereof) in the cell. The labeling peptide component can be a fragment of β galactosidase, for example an enzyme donor (ED), such as a proprietary ED termed a ProLabel (PL) peptide. In some embodiments, the labeling peptide/tag can be other than an ED.

In certain aspects, the present invention comprises a method to assess binding of a compound to a binding site on target peptide in a cell, comprising: (a) providing in the cell a fusion protein comprising (i) the target peptide and (ii) a labeling peptide, wherein the target peptide comprises a destabilizing mutation; (b) incubating a mixture of the cell and the compound for a period sufficient to allow binding of the compound to the binding site of the target peptide and to allow for stabilization of the fusion protein by the binding, then (c) combining the mixture from step (b) with a label that detects an amount of the labeling peptide remaining on the fusion protein after incubating, wherein a change in the amount of labeling peptide detected indicates binding to the target peptide.

The compound, which may be a test compound being evaluated for its binding effect, may be a small molecule, a peptide, or a full-length protein. The compound may be a pharmacological agent or it may be a native ligand for the target peptide. In this situation, one may add a test compound that binds to the native ligand and modulates its binding to the target peptide.

In certain aspects, the present invention comprises a method for measuring binding of a compound to a binding site on a target peptide, as stated above, and the binding site may be one of (a) an ATP binding site, (b) a bromodomain sequence, (c) a catalytically (enzymatic) active site or (d) an allosteric site.

In certain aspects, the present invention comprises a method wherein the labeling peptide is selected from the group consisting of (a) an enzyme donor fragment of β-galactosidase, (b) a peptide having a binding epitope for a secondary label.

In certain aspects, the present invention comprises a method wherein the labeling peptide is an ED having a sequence according to one of SEQ ID NO: 1, SEQ ID NO: 2, or SEQ ID NO: 3.

In certain aspects, the present invention comprises a method wherein the EA has a sequence according to is SEQ ID NO: 4.

In certain aspects, the present invention comprises the above-mentioned methods wherein the cell is a mammalian cell.

In certain aspects, the present invention comprises the above-mentioned methods further comprising the step of carrying out steps (a) through (c) in the absence of the compound to provide a control for determining the change in the amount of labeling peptide detected.

In certain aspects, the present invention comprises the above-mentioned methods wherein the target peptide comprises a mutation which is a truncation, said mutation being outside of the binding site. As described below, the target peptide has been selected so that it has a relatively short half-life unless it is stabilized by binding to a compound. The mutation may involve truncating the target peptide by removing a certain number of amino acids form either the amino terminus, the carboxy terminus or both terminii. The number of amino acids removed will depend on the target peptide being created. It may be for example, up to 5-10 amino acids, 5-20 amino acids, 5-10 amino acids, etc., as long as the binding site is left in the target peptide. Amino acids may be removed from a central domain, such as a domain needed for proper folding. In certain aspects, the present invention comprises a method wherein said target peptide comprises a mutation which is a deletion of at least ten percent of the sequence of the full length protein. In other words, in this embodiment if the native protein is 1000 amino acids long, at least 100 amino acids are removed.

In certain aspects, the present invention comprises a method to assess a small molecule as an inhibitor of binding to a binding site on target peptide in a cell, comprising: (a) providing in said cell a fusion protein comprising (i) said target peptide and (ii) a labeling peptide, wherein the target peptide comprises a destabilizing mutation; (b) adding to a sample well of said cell said compound; (c) incubating said cell and said compound of step (b) for a period sufficient to allow binding of the compound to the binding site of the target peptide and to allow for stabilization of the fusion protein by the binding of the compound, then (d) adding to a sample well of said cell said small molecule; (e) combining, in the sample well, contents of the sample well from step (c) and (d) with a label that detects an amount of the labeling peptide remaining in the cell after said incubating, whereby a change in the amount of labeling peptide detected indicates inhibition of binding of the compound to the target peptide by the small molecule.

In certain aspects, the present invention comprises the above-mentioned methods wherein said compound is one of a small molecule, a peptide, and a full-length protein. In certain aspects, the present invention comprises the above-mentioned methods wherein said small molecule is one of a drug candidate, a peptide, and a full-length protein. In certain aspects, the present invention comprises a method wherein said binding site is one of (a) an ATP binding site, (b) a bromodomain sequence, (c) a catalytic site or (d) an allosteric site.

In certain aspects, the present invention comprises the above-mentioned methods wherein the labeling peptide is (a) an ED or (b) a binding epitope for a labeling peptide. The ED may have according to one of SEQ ID NO: 1, SEQ ID NO:2, or SEQ ID NO:3.

In certain aspects, the present invention comprises a method wherein the assay is carried out without adding a compound, in order to provide a control for said determining said change in the amount of labeling peptide.

In certain aspects, the present invention comprises kits for carrying out the above-mentioned methods. The kits will generally comprise an expression vector for inserting a target of interest and already containing a labeling peptide. In certain aspects, the present invention comprises a kit to study the effect of introduction of compound into a cell comprising (a) a cell comprising: a fusion protein comprising the target and ED fragment of β-galactosidase fragment; (b) compound, (c) EA fragment of β-galactosidase; and (d) a β-galactosidase substrate. In certain aspects, the present invention comprises a kit to study the effect of compound on mediating cellular interactions comprising (a) a cell comprising: a fusion protein comprising the target and ED fragment of β-galactosidase fragment; (b) compound, (c) EA fragment of β-galactosidase; and (d) a β-galactosidase substrate. In certain aspects, the present invention comprises a kit to study effect of small molecule inhibitors on cellular interactions comprising (a) a cell comprising: a fusion protein comprising the target and ED fragment of β-galactosidase fragment; (b) small molecule, (c) EA fragment of β-galactosidase; and (d) a β-galactosidase substrate. In certain aspects, the present invention comprises a kit to monitor interacting interface comprising (a) a cell comprising: a fusion protein comprising the variant sequence lengths of target and ED fragment of β-galactosidase fragment; (b) EA fragment of β-galactosidase; and (c) a β-galactosidase substrate. In certain aspects, the present invention comprises a kit comprising an expression construct encoding a fusion protein comprising a target and ED fragment of β-galactosidase.

BRIEF DESCRIPTION OF THE DRAWINGS

FIG. 7A shows data from PL-Bax, FIG. 7B shows data from PL-Bim, and FIG. 7C shows data from PL-Bak.

DETAILED DESCRIPTION

Overview

As discussed above, truncation of a protein will affect its folding and unfolding, ultimately affecting its functionality. It has been now found that such instability, as well as other factors affecting protein stability within a cell, can be used to measure the effect of stabilization of such a protein. It is recognized that the unstable protein will be degraded by the cell until such time as it forms a complex and can be stabilized from further cellular processes. As binding of both natural compounds (e.g. proteins) and many test compounds occurs through specific binding sequences, certain truncated protein fragments containing the active or allosteric binding sequences can be stabilized through compound binding. Thus, a compound that binds at an active or allosteric site of a protein fragment will form a complex with the fragment and will change its half-life in a cell. This will lead to a greater number of protein molecules in the cell, or greater "protein abundance".

Targeting native or naturally mutated human proteins with small molecule test compounds is an important part of drug development. Thus, monitoring the stability of truncated, destabilized proteins, compounds that bind to the truncated fragments, estimating the interaction interfaces and screening small molecules as inhibitors of cellular binding complexes will have potential applications in drug development against a number of human disorders and represent aspects of the present invention.

A number of small molecules act by binding to the ATP site of the active conformation of their target peptides (e.g. dasatinib, which noncovalently binds to BCR-Abl kinases). By removing portions of the amino and/or carboxyl regions of a target peptide but leaving the ATP binding site, synthetic or natural ATP-competitive molecules can then be tested for binding by measuring the increased stability, and thus residence time in the cell, that such binding causes. An increased concentration of fusion protein bound to the target and carrying the PL will be measured by adding the EA, giving us an indication of the binding sequence which can further be characterized by known biophysical and biological approaches.

In summary, the present methods are carried out so as to measure the amount (e.g. concentration, or abundance) of a target peptide that remains in a cell after a predetermined time that is chosen to distinguish a target peptide, which is bound to an enzyme fragment for detection, that has bound a test compound and thus been stabilized against cellular turnover, from a target peptide that is not bound to the binding entity and is degraded by cellular machinery, such degradation also removing the enzyme fragment label.

Figure 1:
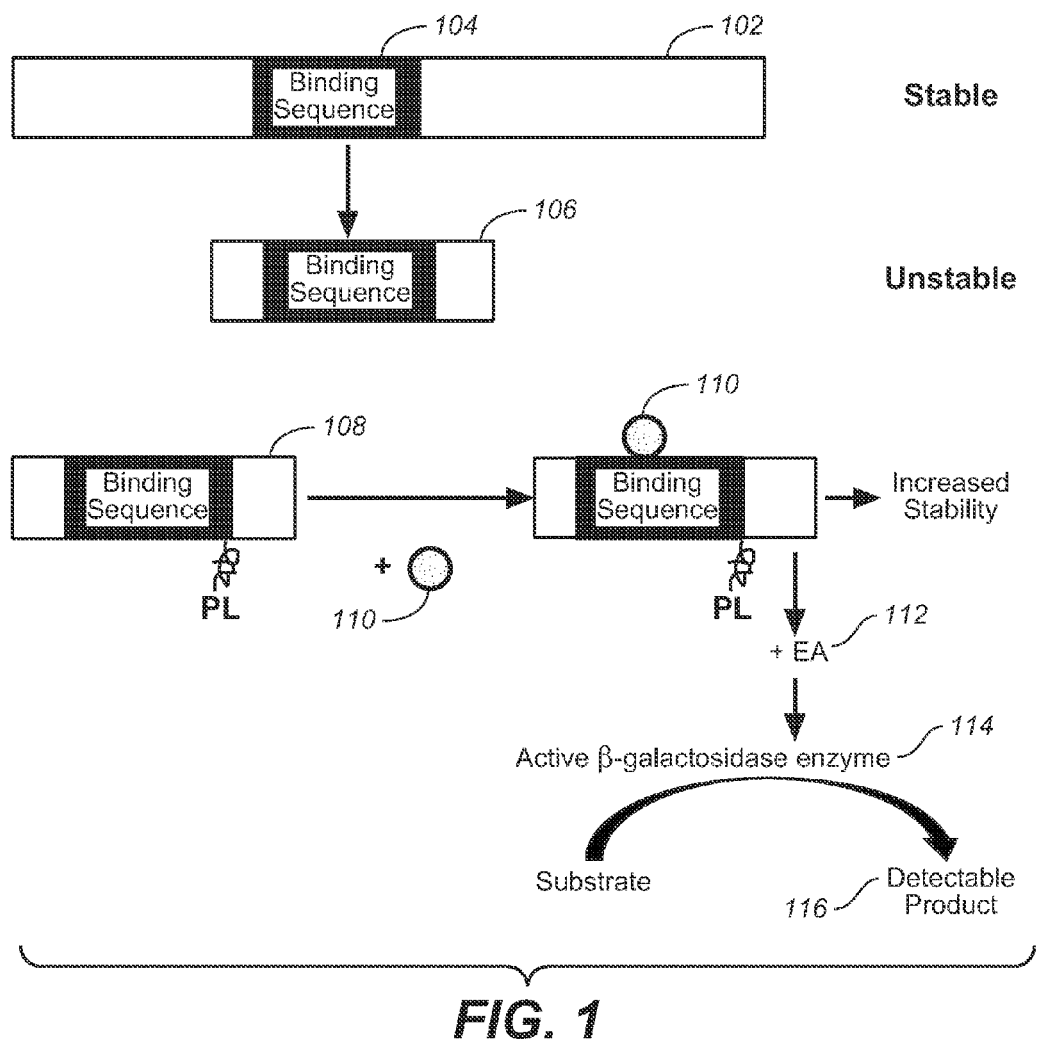
FIG. 1 is a schematic representation of an embodiment of the present assay showing how a fragment of a stable protein is unstable, stabilized by binding of a compound to binding site, and detected with increased abundance.
Figure 2:
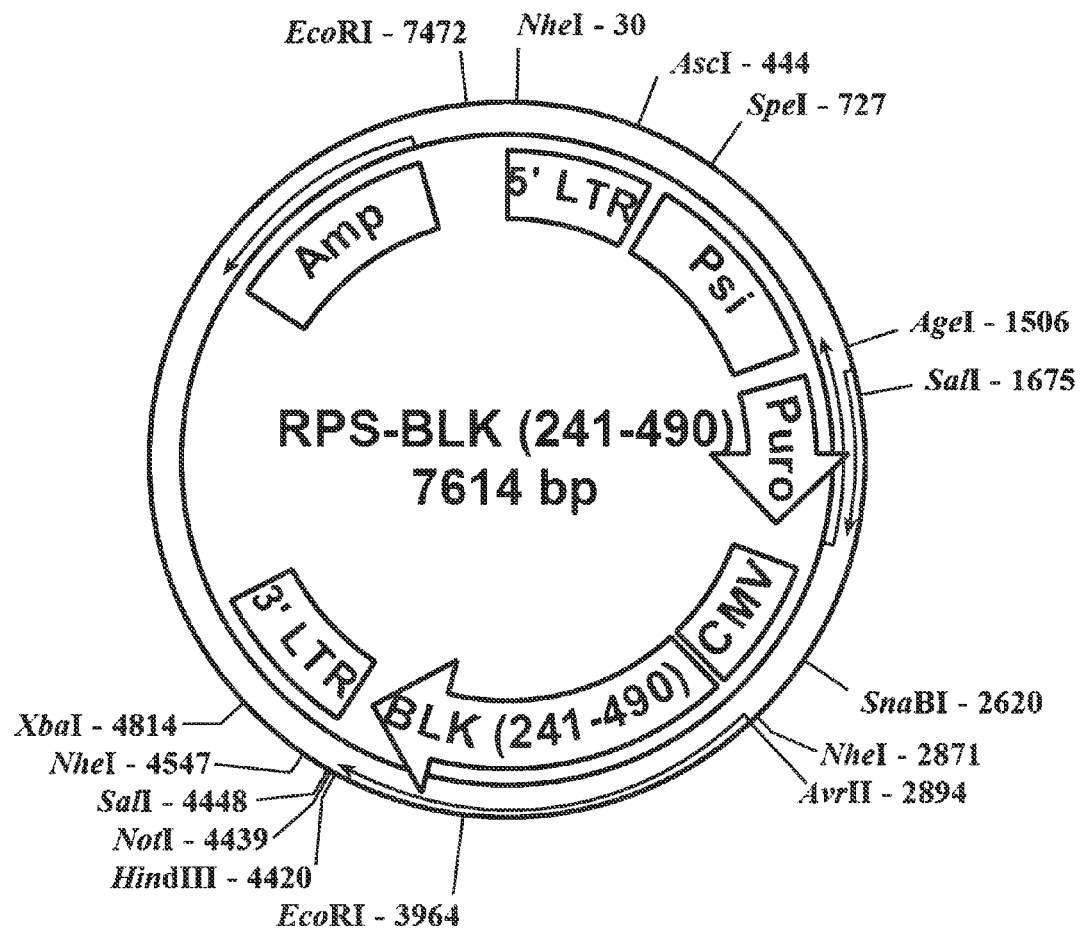
FIG. 2 is a plasmid map of RPS-BLK (241-490) for expressing a BLK construct of amino acids 241-490.

Referring now to FIG. 1, a full length protein 102 containing an amino acid sequence or protein domain 104, that participates in binding is generally stable in a cell and has a consistent, measurable half life. The binding sequence 104, e.g. a ligand binding site such as an ATP binding site, or a protein-protein interaction site such as an α1 helix of BAX, may be anywhere within the primary sequence of the protein. It may be a contiguous sequence in primary structure or it may exist as amino acids in proximity in tertiary structure. The binding sequence will generally be on the surface of the protein. In the present assay, the protein 102 is truncated as shown at 106, where truncation may occur from the N terminus, the C terminus, or, as shown here, both terminii. The binding sequence 104, however, is still present in the truncated target peptide. Because of these alterations, the cell will degrade the truncated protein (peptide) more rapidly. In the present assay, the truncated peptide 106 is fused with a small fragment of β-galactosidase (PL enzyme donor in this example) as shown at 108. Binding of a compound 110 to the truncated peptide 108 will increase the stability of the truncated fragment, an effect which can then be estimated by incubating the sample with a complementing β-galactosidase fragment, an enzyme acceptor or EA, shown at 112. The complementation of ED and EA results in an active enzyme (shown at 114) which will convert the substrate into a measurable product (shown at 116). The test compound 110 itself may stabilize the truncated peptide, or, in certain embodiments, the test compound 110 mediates the binding of the truncated peptide to a cognate binding partner, and this binding to the binding partner stabilizes the truncated peptide. The compound may increase or decrease such binding and affect stability of the truncated peptide rather than directly stabilizing the truncated peptide. The ED label on the truncated peptide serves only for labeling and not for stabilization.

DEFINITIONS

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. Generally, nomenclatures utilized in connection with, and techniques of, cell and molecular biology and chemistry are those well known and commonly used in the art. Certain experimental techniques, not specifically defined, are generally performed according to conventional methods well known in the art and as described in various general and more specific references that are cited and discussed throughout the present specification.

In accordance with the present invention there may be employed conventional molecular biology, microbiology, and recombinant DNA techniques within the skill of the art. Such techniques are explained fully in the literature. See, e.g. Maniatis, Fritsch & Sambrook, "Molecular Cloning: A laboratory Manual (1982); "DNA Cloning: A Practical Approach, "Volumes I and II (D. N. Glover ed. 1985); "Oligonucleotide synthesis" (M. J. Gait ed. 1984); "Nucleic Acid Hybridization" (B. D. Hames & S. J. Higgins eds. (1985)); "Transcription and Translation" (B. D. Hames & S. J. Higgins eds. (1984)); "Animal Cell Culture" (R. I. Freshney, ed. (1986)); "Immobilized Cells and Enzymes" (IRL Press, (1986)); B. Perbal, "A Practical Guide to Molecular Cloning" (1984).

It is noted that, as used herein and in the appended claims, the singular forms "a", "an", and "the" include plural references unless the context clearly dictates otherwise. It is further noted that the claims may be drafted to exclude any optional element. As such, this statement is intended to serve an antecedent basis for use of such exclusive terminology as "solely"" "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the feature of any of the other several embodiments without departing from the scope or spirit of the present invention. Any recited method can be carried out in the order of events recited or in any other order which is logically possible.

For purposes of clarity, the following terms are defined below.

The term "peptide" as used herein refers to any polymer compound produced by amide formation between an α-carboxyl group of one amino acid and an α-amino group of another group.

The term "BCL2" is used in its scientifically accepted sense to refer to a family of proteins whose members contain at least one of the four conserved α-helical motifs known as the Bcl-2 homology (BHI-4) domains. The family is further classified into functional groups, the antiaptotic and the proapoptotic members, as described in Szegezdi et al., "Bcl-2 family on guard at the ER." Am J Physiol Cell Physiol, 2009; 296: C941-C953.

Similarly, the terms BIM, BAK and BAX refer to members of the BCL2 family. Multidomain proapoptotic BAX and BAK are essential effectors. The activator BH3s, tBID/BIM/PUMA, attack and expose the a1 helix of BAX, as described e.g. in Kim et al., "Stepwise Activation of BAX and BAK by tBID, BIM, and PUMA Initiates Mitochondrial Apoptosis," Molecular Cell 36, 487-499, Nov. 13, 2009

The term "BLK" is used in its scientifically accepted sense to refer to B-lymphocyte kinase, NCBI reference sequence NP_001706, also known as tyrosine-protein kinase Blk [Homo sapiens]. Variants of this sequence are found in the protein tyrosine kinase (PTK) family; Lck and Blk kinases; catalytic (c) domain. The PTKc family is part of a larger superfamily that includes the catalytic domains of other kinases such as protein serine/threonine kinases, RIO kinases, and phosphoinositide 3-kinase (PI3K).

The term "MEK" is used in its scientifically accepted sense to refer to a protein kinase that phosphorylates the ERK gene product. The MEK subfamily of protein kinases is part of a larger superfamily that includes the catalytic domains of other protein serine/threonine kinases, protein tyrosine kinases, RIO kinases, aminoglycoside phosphotransferase, choline kinase, and phosphoinositide 3-kinase. The mitogen-activated protein (MAP) kinase signaling pathways are important mediators of cellular responses to extracellular signals. The pathways involve a triple kinase core cascade comprising the MAP kinase (MAPK), which is phosphorylated and activated by a MAPK kinase (MAPKK or MKK), which itself is phosphorylated and activated by a MAPK kinase kinase (MAPKKK or MKKK). MEK1 and MEK2 are dual-specificity PKs that phosphorylate and activate the downstream targets, ERK (extracellular signal-regulated kinase) 1 and ERK2, on specific threonine and tyrosine residues.

The term "protein" as used herein refers to polypeptides of specific sequence of more than about 50 residues. While all proteins are peptides, the term "peptide" generally refers to a fragment of a protein; the term "fusion protein" is used to refer to both fusion proteins and fusions with peptides, such as a fusion with a labeling peptide, e.g. an ED.

The term "fusion protein" as used herein refers to a protein created through genetic engineering from two or more proteins/peptides. In general, this is achieved by creating a "fusion gene", a nucleic acid that encodes the fusion protein. For example, a fusion gene that encodes a fusion protein may be made by removing the stop codon from a first DNA sequence encoding the first protein, then appending a DNA sequence encoding the second protein in frame. The resulting fusion gene sequence will then be expressed by a cell as a single fusion protein. Fusion proteins may include a linker (or "spacer") sequence which can promote appropriate folding and activity of each domain of the fusion protein. Fusion proteins may also include epitope tags for identification (e.g., in western blots, immunofluorescence, etc.) and/or purification. Non-limiting examples of epitope tags in current use include: HA, myc, FLAG, and 6-HIS (SEQ ID NO: 19).

The term "amino acid" as used herein is intended to include not only the L-, D- and nonchiral forms of naturally occurring amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine), but also modified amino acids, amino acid analogs, and other chemical compounds which can be incorporated in conventional oligopeptide synthesis, e.g., 4-nitrophenylalanine, isoglutamic acid, isoglutamine, ε-nicotinoyl-lysine, isonipecotic acid, tetrahydroisoquinoleic acid, α-aminoisobutyric acid, sarcosine, citrulline, cysteic acid, t-butylglycine, t-butylalanine, phenylglycine, cyclohexylalanine, β-alanine, 4-aminobutyric acid, and the like. The amino acid sequences are given in one-letter code (A: alanine; R: arginine; N: asparagine; D: aspartic acid; C: cysteine; Q: glutamine; E: glutamic acid; G: glycine; H: histidine; I: isoleucine; L: leucine; K: lysine; M: methionine; F: phenylalanine; P: proline; S: serine; T: threonine; W: tryptophan; Y: tyrosine; V: valine; X: any residue). $NH_2$ refers to the free amino group present at the amino terminus of a polypeptide. COOH refers to the free carboxy group present at the carboxy terminus of a polypeptide in keeping with standard polypeptide nomenclature, (J Biol. Chem. 243 (1969), 3352-59) is used.

The term "vector" as used herein refers to is a replicon, such a plasmid, phage or cosmid, to which another DNA segment may be attached so as to bring about the replication of the attached segment.

A cell has been "transformed" or "transfected" by exogenous or heterologous DNA when such DNA has been introduced inside the cell. The transforming DNA may or may not be integral (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lies or clones comprised of a population of cells derived from a single cell or common ancestor by mitosis. A "cell line" is a clone of a primary cell that is capable of stable growth in vitro for many generations.

As used herein, the term "expression system" refers to any suitable exogenous system for expressing the receptor components in the cell. For example, exogenous expression of receptor components by a cell as provided herein can result from the introduction of the nucleic acid sequences encoding the receptor component or a fusion protein comprising a receptor component in an expression vector. As used herein, the term "fusion protein" refers to a reporter component that is fused to a heterologous protein or protein fragment using recombinant technology.

The term "target" as used herein refers to various macromolecules present in a cell such as DNA, RNA, lipids, proteins and carbohydrates or their constituent monomers. The term "target peptide" refers to a target peptide that has been modified by truncation or the like as described below, is labeled with a β-galactosidase fragment (preferably PL) and is being tested with a test compound, such as a small molecule, or another protein, or a combination of a small molecule and a protein partner. Exemplary target peptides include kinases, actins, chaperonins, hsp proteins, and polymerases, which have ATP binding sites, and G proteins and dynamin, which bind GTP.

The term "small molecule" is art-recognized and refers to a composition which has a molecular weight of less than 35 about 2000 amu, or less than about 1000 amu, and even less than about 500 amu. Small molecules may be, for example, nucleic acids, peptides, polypeptides, peptide nucleic acids, peptidomimetics, carbohydrates, lipids or other organic (carbon containing) or inorganic molecules. Many pharmaceutical companies have extensive libraries of chemical and/or biological mixtures, often fungal, bacterial, or algal extracts, which can be screened with any of the assays of the invention. The term "small organic molecule" refers to a synthetic or purified natural small molecule that is often identified as being an organic or medicinal compound, and does not include molecules that contain nucleic acids, peptides or polypeptides.

The term "binding" as used herein refers to the binding of small molecules, proteins or compound to the known proteins in a cell. The terms "binding partner" or "member of a binding pair" refer to molecules that specifically bind other molecules to form a binding complex such as antibody-antigen, lectin-carbohydrate, nucleic acid-nucleic acid, biotin-avidin, etc. In particularly preferred embodiments, the binding is predominantly mediated by non-covalent (e.g. ionic, hydrophobic, etc.) interactions and is between a small molecule and its target and/or two proteins that specifically bind to each other during a cellular process.

The term "protein abundance" is used as described herein, and in a commonly accepted sense, as described, e.g. in Ivanic J, Yu X, Wallqvist A, Reifman J (2009) "Influence of Protein Abundance on High-Throughput Protein-Protein Interaction Detection," PLoS ONE 4(6): e5815. doi:10.1371/journal.pone.0005815. Protein abundance can be regarded as the number of protein or peptide molecules in a cell at a given time.

The term "destabilizing mutation" means a mutation in a peptide or protein sequence that causes an alteration in the stability of the peptide or protein in the cell, that is, the likelihood of its degradation or aggregation within a certain time period. Mutations may include amino acid deletions, additions or substitutions. The mutation generally will cause misfolding of the peptide or protein. The stability of the peptide or protein in a cell may also refer to the duration of time that the protein is present in the cell before being removed or degraded by cellular machinery. Protein or peptide stability can be measured in vivo (i.e. in a cell) by a number of methods, such as disclosed e.g. in Ghaemmaghami et al., "A quantitative, high-throughput screen for protein stability," PNAS Jul. 18, 2000 vol. 97 no. 15 8296-8301 or Ignatova et al. "Monitoring protein stability and aggregation in vivo by real-time fluorescent labeling," *PNAS Jan.* 13, 2004 vol. 101 no. 2 523-528. Thus whether or not a mutation is a destabilizing mutation can be determined by comparing the mutated protein to the non-mutated protein and observing that the mutated protein has a half-life in the cell that is at least 10% or more shorter than that of the non-mutated protein. In some cases, the half-life may be at least 20% or more shorter than that of the non-mutated protein or 30% or more shorter than that of the non-mutated protein. In some cases, the destabilizing mutation will result in a peptide having a half-life of less than 3 hrs inside of a cell.

In certain aspects, the term "destabilizing mutation" refers to mutations which are truncations in which at least 5 amino acids are removed from either or both of the N terminal region or the C terminal region of a target peptide. Further, it may also refer to truncation from either or both of the N terminus or the C terminus which leads to the destabilization of the target peptide inside of a cell. As explained below, in the present method, the destabilizing mutation is not to the binding site of the target peptide.

The term "labeling peptide" means a peptide having essentially no secondary structure (i.e. random coil) and which functions as a label for detection of a protein or protein fragment (e.g. target peptide) fused thereto and having essentially no effect on the stability of the target peptide to which it is fused. The labeling peptide will generally be less than 100 amino acids in length. It may itself function as a label, or it may provide an epitope for antibody recognition. As explained below, the labeling peptide is selected so as not to affect the stability or half life of a fusion partner of the labeling peptide.

The term "target peptide" refers to a protein or protein fragment which is the target of binding modulated by a test compound in the present assay. The target peptide will have a native site which provides a binding site for the test compound or that is a binding site for another cellular component wherein the test compound modulates. For example, the target peptide may have a catalytic site, a co-factor binding site, an allosteric regulatory site, etc. The binding site may also be a binding site for a native ligand. A native ligand is a cellular molecule that binds to the binding site of the target peptide as part of a cellular process. Examples are enzyme catalytic site-substrate, enzyme regulatory site-regulator, receptor-ligand, G-protein accessory proteins, etc.

The term "test compound" is used in a general sense to refer to a small molecule, macromolecule or other material that has a property of binding to a particular target peptide at a binding site. The test compound is generally not normally found in the cell where it is tested at the concentration being tested. The test compound may produce a positive test result of binding or a negative test result of not binding; binding may also be quantified, according to the present methods. More than one test compound may be used, in that a test compound may be used as a reference compound known to bind to a specific site, such as a catalytic site, and ATP binding sire, etc. on a target peptide. The test compound will in some cases bind non-covalently to the binding site; in some cases it will bind covalently to the binding site.

The term "sample well" means any fluid container, and includes wells in a microtiter plate, various test tubes (e.g. Eppendorf tubes), chambers in a microfluidic device, etc.

The term "ED", as is known in the art, means an enzyme donor fragment for use in a β-galactosidase enzyme fragment complementation assay. Examples of EDs are given below.

The term "binding site" refers to a sequence or cluster of residues on a target where the target binds to another molecule. Binding sites on proteins are well known and characterized. They are generally specific to a certain ligand or binding partner. They can be identified on a sequence basis by tools such as PPSearch, at EMBL-EBI. Exemplary binding sites are (a) nucleotide (e.g. ATP) binding site, (b) a bromo-domain sequence, (c) a catalytic site or (d) an allosteric site.

General Methods and Materials
Enzyme Fragment Complementation

In certain embodiments, the present presently disclosed methods and materials employ the wild-type *E. coli* β-galactosidase upon which the enzyme fragment complementation (EFC) system is based. The wild-type *E. coli* β-galactosidase is encoded by the *E. coli* lacZ gene.

The β-galactosidase enzymes and its fragments (See, U.S. Pat. No. 4,708,929) are required to have a number of characteristics. The fragments are substantially inactive individually, in that there is little, if any, background with only one fragment present in the presence of substrate. Secondly, the fragments have sufficient affinity for each other, that in the absence of other binding, e.g. by entities fused to the fragments, the fragments will combine to provide an active enzyme. The small fragment ("ED" or "PL") may be designed artificially and will not interfere with the biological activity of the gene or protein to which it is fused. The resulting fusion protein, as has been determined here, will fold properly and retain sites of activity, including enzyme activity, binding activity to other proteins, translocation capability, etc. ED will usually be at least about 37, usually at least about 40 amino acids, and usually not more than about 110, more usually not more than about 90.

In certain embodiments, the employed β-galactosidase complementation system is one that is made up of two or more β-galactosidase fragments or variants thereof. For example, in certain embodiments, the complementation system includes a first and second fragment of β-galactosidase (e.g., an α and ω fragment). In yet other embodiments, the complementation system may include more than two β-galactosidase fragments, such as a first, second and third β-galactosidase fragments (e.g., an α, β and ω fragment).

In a preferred aspect, small fragment of β-gal (also the signal producing peptide) will be referred to as the enzyme donor (ED). The signal producing peptide is one of a pair of fragments of an enzyme that is reconstituted when the two fragments, the enzyme donor ("ED") and the enzyme acceptor ("EA") complex together. The ED will be a fragment of an enzyme that can be complemented with another fragment, the EA, to form an active enzyme. The ED fragment of the fusion protein will complex with the EA fragment as a result of the affinity of the fragments for each other.

In other embodiments, the complementing fragments are high affinity fragments. High affinity components are generally two fragments of an enzyme with the fragments having sufficiently high affinity such that they can spontaneously bind to each other and reform a fully functional enzyme or enzyme subunit. Typically, at least 5% of enzymatic activity of the native enzyme is achieved when mixed under appropriate conditions in solution, sometimes about 10, 20, 30, 40, 50, 60, 70, 80, 90, 95, 99, or 100% of the enzymatic activity of the native enzyme. Determination of such activity can be performed using routine methods with the concentration at which the complemented enzyme and parental enzyme are compared typically being the same with a range of, e.g., between $10^{-3}$ to $10^{-6}$M. High affinity components permits monitoring of the presence, absence, or increase of the complementing fragments as they form a complex with the interacting partner. For example, if one complementing fragment is present in the fusion protein (fused to the target of interest) and forms a complex with the test compound then the incubation with the second fragment after lysis of the cell will result in detectable enzymatic activity, thus permitting the analysis of cellular interactions. Accordingly, if the amount of high affinity components increases in the assay system, then the amount of detectable enzymatic activity will increase proportionally. Typically, large increases in the amount of activity are detectable up to a 1:1 reporter component ratio. See e.g., the experimental section below, as well as U.S. patent application Ser. No. 11/132,764 filed on May 18, 2005 for a review of such a rational approach as employed with an initial high affinity .beta.-galactosidase complementation reporter system.

In some embodiments, the fusion protein comprises a truncated fragment of target of interest and high affinity ED fragment, wherein the target of interest is a protein kinase and the truncated fragment consists of the ATP-binding sequence. In some embodiments, the truncated protein fragment consists of non ATP binding sequence. The test compound can be an ATP-competitive molecule, allosteric modulators or a kinase binding molecule. In some embodiments, the fusion protein comprises a truncated fragment of target of interest and low affinity ED fragment.

Various other indicator enzymes are also known to fulfill these criteria and additional enzymes may be developed in accordance with known technologies. Indicator enzymes that fit these criteria include split luciferase, GFP, ribonuclease A (See, U.S. Pat. No. 4,378,428), where the smaller fragment may come from the amino or carboxy terminus or internally, β-lactamase WO 00/71702 and 01/94617 and Wehrman, et al., Proc. Natl. Acad. Sci. 2002, 99, 3469-74, or enzymes that have small peptide cofactors, such as adenovirus proteases (See, U.S. Pat. No. 5,935,840).

In a specific embodiment, the α peptide employed is one that complements the ω peptide robustly in mammalian cells. The high affinity minimal α peptide permits sensitive, accurate analysis of cellular interaction events between various intracellular entities with only a minimum of interactions required for detection. Exemplary high affinity α peptides (enzyme donors) include

```
(Wild-type ED)                               SEQ ID NO. 1
MGVITDSLAVVLQRRDWENPGVTQLNRLAAHPPFASWRNSEEARTDRPS

QQL (Prolabel, or "PL" ED)                       SEQ ID NO. 2
NSLAVVLQRRDWENPGVTQLNRLAAHPPFASWRNSEEARTDR,
and (W34Y, a modified ED)                        SEQ ID NO. 3
MGVITDSLAVVLQRRDWENPGVTQLNRLAAHPPFASYRNSEEARTDRPS

QQL.
```

Another applicable ED is termed enhanced prolabel, SEQ ID NO. 4 below:

```
                                             (SEQ ID NO. 4)
   NSLAVVLQRRDWENPGVTQLNRLAAHPPFASWRNSEEARTDR
```

The enzyme fragments can be coupled to the peptide target of interest using any suitable method. Thus, the enzyme fragments and one or more targets of interest can be linked either directly or via a linker. Typically, the linker is covalent. For example, when the enzyme fragment and the target of interest are proteins, methods known in the art for linking peptides can be employed. In one preferred embodiment, the enzyme fragment and the target of interest comprise a fusion protein that includes the enzyme fragment and the target being assayed.

Aspects of the methods include the use of a reduced-affinity enzyme complementation reporter system which is extensively described in the aforementioned references, U.S. Pat Appln. No. 20070275397, Pub. Date Nov. 29, 2007 and U.S. Pat Appln. No. 20100285451, Pub. Date Nov. 11, 2010 whose method section is specifically incorporated by reference as if set forth in its entirety herein.

Embodiments of the reduced-affinity enzyme complementation reporter systems are characterized by providing a high signal-to-noise ratio.

Aspects of the method include the use of a first β-galactosidase fragment (also known as an enzyme donor or α fragment) that is a variant minimal N-terminal β-galactosidase peptide. By minimal N-terminal β-galactosidase peptide is meant that the peptide has an amino acid sequence that is found in the N-terminal region of a wild-type β-galactosidase protein, e.g., a sequence that starts within about 10 residues of the N-terminus, such as within about 5 residues of the N-terminus of a wild-type β-galactosidase protein. As the first β-galactosidase fragments of this embodiment are minimal, they are, in certain embodiments, about 60 amino acids or less in length, such as about 55 amino acids in length or less, including about 50 amino acids or less in length, e.g., 49 amino acids or less in length, 48 amino acids or less in length, etc.

In certain embodiments, the second β-galactosidase fragment is a deletion mutant that is missing aa 11-41 of the wild type E. coli β-galactosidase protein (e.g., as described in Langley et al., Proc. Nat'l Acad. Sci. USA (1975) 72: 1254-1257), which fragment is known as the M15 acceptor or ω fragment. Other specific acceptors (i.e., co-fragments) of interest include, but are not limited to: the M112 dimer, a deletion of amino acids 23-31 within β-galactosidase (Lin, Villarejo and Zabin, 1970, Biochem. Biophys. Res. Common. 40:249; Celeda and Zabin, 1979, Biochem. 18:404; Welphy, Fowler and Zabin, 1981, J. Biol. Chem. 256:6804; Langley et al., 1975, Proc. Natl. Acad. Sci. USA 72:1254).

One exemplary ω peptide sequence is set forth below (SEQ ID NO. 5)

MGVITDSLAVVARTDRPSQQLRSLNGEWRFAWFPAPEAVPESWLECDLPEADTVVVPS

NWQMHGYDAPIYTNVTYPITVNPPFVPTENPTGCYSLTFNVDESWLQEGQTRIIFDGVNS

AFHLWCNGRWVGYGQDSRLPSEFDLSAFLRAGENRLAVMVLRWSDGSYLEDQDMWR

MSGIFRDVSLLHKPTTQISDFHVATRFNDDFSRAVLEAEVQMCGELRDYLRVTVSLWQG

ETQVASGTAPFGGEIIDERGGYADRVTLRLNVENPKLWSAEIPNLYRAVVELHTADGTLI

EAECDVGFREVRIENGLLLLNGKPLLIRGVNRHEHHPLHGQVMDEQTMVQDILLMKQN

NFNAVRCSHYPNHPLWYTLCDRYGLYVVDEANIETHGMVPMNRLTDDPRWLPAMSER

VTRMVQRDRNHPSVIIWSLGNESGHGANHDALYRWIKSVDPSRPVQYEGGGADTTATD

IICPMYARVDEDQPFPAVPKWSIKKWLSLPGETRPLILCEYAHAMGNSLGGFAKYWQAF

RQYPRLQGGFVWDWVDQSLIKYDENNPWSAYGGDFGDTPNDRQFCMNGLVFADRTP

HPALTEAKHQQQFFQFRLSGQTIEVTSEYLFRHSDNELLHWMVALDGKPLASGEVPLDV

APQGKQLIELPELPQPESAGQLWLTVRVVQPNATAWSEAGHISAWQQWRLAENLSVTL

PAASHAIPHLTTSEMDFCIELGNKRWQFNRQSGFLSQMWIGDKKQLLTPLRDQFTRAPL

DNDIGVSEATRIDPNAWVERWKAAGHYQAEAALLQCTADTLADAVLITTAHAWQHQG

KTLFISRKTYRIDGSGQMAITVDVEVASDTPHPARIGLNCQLAQVAERVNWLGLGPQEN

YPDRLTAACFDRWDLPLSDMYTPYVFPSENGLRCGTRELNYGPHQWRGDFQFNISRYS

QQQLMETSHRHLLHAEEGTWLNIDGFHMGIGGDDSWSPSVSAEFQLSAGRYHYQLVW

CQK

A range of methods are available to measure the enzyme activity of β-galactosidase which include live cell flow cytometry and histochemical staining with the chromogenic substrate 5-bromo-4-chloro-3-indolyl β-D-galactopyranoside (X-Gal). see e.g., Nolan et al., Proc. Natl. Acad. Sci., USA, 85: 2603-2607 (1988); and Lojda, Z., Enzyme Histochemistry: A laboratory Manual, Springer, Berlin, (1979).

Assays of β-gal activity as described in Mohler and Blau, Proc. Natl. Acad. Sci., 93: 12423-12427 (1996) may be used. In one embodiment, intracellular analyses may be conducted by fixing cells and staining with the indigogenic substrate X-gal. Fixed cells also can be analyzed by assaying for β-gal activity by fluorescence histochemistry using an azo dye in combination with either X-gal or 5-bromo-6-chloro-3-indolyl β-D-galactopyranoside (5-6-X-Gal). A combination of interest is the azo dye red violet LB (Sigma Chemicals, St. Louis, Mo.) and 5-6-X-Gal, referred to as Fluor-X-gal. For this combination, fluorescence micrographs can be obtained on a fluorescence dependent fluorescence to be visualized simultaneously with two or more other fluorescent signals.

Vital substrates for β-gal, which can be used in living cells, are also encompassed by the presently disclosed methods and materials. For example, a fluorogenic substrate, resorufin β-galactosidase bis-aminopropyl polyethylene glycol 1900 (RGPEG) has been described. Minden (1996) BioTechniques 20(1): 122-129. This compound can be delivered to cells by microinjection, electroporation or a variety of bulk-loading techniques. Once inside a cell, the substrate is unable to escape through the plasma membrane or by gap junctions. Another vital substrate that can be used in the practice of the presently disclosed methods and materials is fluorescein di-β-D-galactopyranoside (FDG), which is especially well-suited for analyses for analysis by fluorescence-activated cell sorting (FACS) and flow cytometry. Nolan et al., Proc. Natl. Acad. Sci, USA, 85:2603-2607 (1988) and Rotman et al. (1963) Proc. Natl. Acad. Sci, USA 50:1-6.

β-galactosidase may also be detected using a chemiluminescence assay. For example, cells containing β-galactosidase fusions are lysed (with or without contacting with a crosslinking agent) in a mixture of buffers containing Galacton Plus substrate from a Galactolight Plus assay kit (Tropix, Bedford Mass.) Bronstein et al, J. Biolumin. Chemilumin., 4:99-111 (1989). After addition of Light Emission Accelerator solution, luminescence is measured in a luminometer or a scintillation counter.

Representative substrates that are suitable for spectrophotometric or fluorometric analysis include, but are not limited to: p-aminophenyl-β-D-galactopyranoside; 4-methylumbelliferyl-β-D-galactopyranoside; mapthyl-AS-B1-β-D-galactopyranoside; 1-napthyl-β-D-galactopyranoside; 2-napthyl-β-D-galactopyranoside monohydrate; O-nitrophenyl-β-D-galactopyranoside; and phenyl-β-D-galactopyranoside, 5-bromo-4-chloro-3-indolyl-β-D-galactopyranoside, resorufin β-D-galactopyranoside, 7-hydroxy-4-trifluoromethyl coumarin, Ω-notrostyryl-β-D-galactopyranoside and fluorescein-β-D-galactopyranoside. See e.g., U.S. Pat. No. 5,444, 161 for exemplary substrates.

Association of components of the complementation systems disclosed herein will depend upon factors in solution, such as pH, ionic strength, concentration of components of the assay, and temperature. Assay solutions can be designed and developed for a particular system. The reporter systems disclosed herein can be used to conduct assays in solutions, such as buffered cell free solutions, cell interiors, solutions of cells, solutions of cell lysates and solutions of cell fractions, such as nuclear fractions, cytoplasmic fractions, mitochondrial fractions and membrane fractions. Methods for preparing assay solutions, such as enzyme assay solutions, cell extracts and cell suspensions, known in the art may be used. For example, physiologically compatible buffers such as phosphate buffered saline may be used. See for example, the series, Methods in Enzymology, Academic Press, New York.

In some embodiments, the first and second reporter components are each fluorescent proteins and the detectable signal results from fluorescence resonance energy transfer (FRET). Luminescent proteins may also be employed. Thus, the first complementing component is a luminescent protein and the second complementing component is fluorescent proteins and the detectable signal results from bioluminescence resonance energy transfer (BRET). Any suitable fluorescent protein can be used including, but not limited to green, red, cyan and yellow fluorescent proteins. In one example, the luminescent protein is a *Renilla* luciferase or a firefly luciferase.

In another aspect, provided herein is a nucleic acid sequence encoding SEQ ID NO: 1, SEQ ID NO: 2, SEQ ID NO: 3, SEQ ID NO: 4 or SEQ ID NO: 5, a vector comprising the nucleic acid sequence, and a cell comprising the nucleic acid sequence or the vector. Also provided herein is a polypeptide encoded by the nucleic acid sequences provided herein. Specifically, provided herein is a polypeptide comprising the polypeptide encoded by SEQ ID NO: 1, SEQ ID NO: 2, SEQ ID NO: 3 SEQ ID NO: 4 or SEQ ID NO: 5.

Vectors

In certain embodiments, the fusion gene constructs of the invention are introduced into cells to assay for cellular interactions. The fusion gene constructs may also contain promoters and other transcriptional and/or translational regulatory sequences that are normally associated with the gene encoding the target of interest. The fusion gene construct may be introduced into cells by any method of nucleic acid transfer known in the art, including, but not limited to, viral vectors, transformation, co-precipitation, electroporation, neutral or cationic liposome-mediated transfer, microinjection or gene gun. Viral vectors of interest include, but not limited to: retroviruses, poxviruses, herpesviruses, adenoviruses, and adeno-associated viruses. In certain embodiments, retroviral vectors are employed, which are capable of stable integration into the genome of the host cell. For example, retroviral constructs encoding integration and packaging signals, drug resistance markers and one or more fusion genes of interest are useful in the practice of certain embodiments of the invention.

Different fusion gene constructs encoding unique fusion protein may be present on separate nucleic acid molecules or on the same nucleic acid molecule. The present fusion gene construct or fusion proteins may be introduced into cultured cells, animal cells in vivo, animal cells ex vivo, or any other type of cell in which it is desired to study cellular interactions.

Any suitable expression system can be used to express the reporter components in situ. Transformation may be achieved using viral vectors, calcium phosphate, DEAE-dextran, electroporation, cationic lipid reagents, or any other convenient technique known in the art. The manner of transformation useful in the present invention are conventional and are exemplified in Current Protocols in Molecular Biology (Ausubel, F. M., et al., eds. 2000). Exogenous expression of the receptor components can be transient, stable, or some combination thereof. Exogenous expression can be enhanced or maximized by co-expression with one or more additional proteins, e.g., HIV rev. Exogenous expression can be achieved using constitutive promoters, e.g., SV40, CMV, and the like, and inducible promoters known in the art. Suitable promoters are those which will function in the cell of interest. In one embodiment, the expression vector is a retroviral vector.

The expression construct is produced in accordance with conventional ways, as described in various laboratory manuals and by suppliers of vectors that are functional in numerous hosts. See, for example, Sambrook, Fritsch & Maniatis, "Molecular Cloning: A Laboratory Manual," Second Edition (1989) Cold Spring Harbor Laboratory Press, Cold Spring Harbor, N.Y. (herein "Sambrook et al., 1989"); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

It should be understood that the site of integration of the expression construct, if integrated into a host chromosome, would affect the efficiency of transcription and, therefore, expression of the fusion protein. One may optimize the efficiency of expression by selecting for cells having a high rate of transcription, one can modify the expression construct by having the expression construct joined to a gene that can be amplified and coamplifies the expression construct, e.g. DHFR in the presence of methotrexate, or one may use homologous recombination to ensure that the site of integration provides for efficient transcription. By inserting an insertion element into the genome, such as Cre-Lox at a site of efficient transcription, one can direct the expression construct to the same site. In any event, one will usually compare the enzyme activity from cells in a predetermined environment to cells in the environment being evaluated.

The gene encoding the fusion protein will be part of an expression construct. The gene is positioned to be under transcriptional and translational regulatory regions functional in the cellular host. In many instances, the regulatory regions may be the native regulatory regions of the gene encoding the protein that forms the EC (expression construct), where the fusion protein may replace the native gene. The site of the gene in an extrachromosomal element or in the chromosome may vary as to transcription level. Therefore, in many instances, the transcriptional initiation region will be selected to be operative in the cellular host, but may be from a virus or other source that will not significantly compete with the native transcriptional regulatory regions or may be associated with a different gene from the gene for the EC, which gene will not interfere significantly with the transcription of the fusion protein.

Vectors that may be used include viruses, plasmids, cosmids, phagemids, YAC, BAC and HAC. Other components of the vector may include origins of replication for one or more hosts, expression constructs for selection, including antibiotic resistance, proteins providing for a signal, etc., integration sequences and enzymes providing for the integration, multiple cloning sites, expression regulatory sequences, expression construct for a protein of interest. Commercially available vectors have many or all of these capabilities and may be used to advantage.

By way of example, nucleotide sequence of the plasmid cloning vector pCMV-PL-C1 (SEQ ID NO. 6), having a CMV promoter, is shown below:

```
   1  TAGTTATTAA TAGTAATCAA TTACGGGGTC ATTAGTTCAT AGCCCATATA
  51  TGGAGTTCCG CGTTACATAA CTTACGGTAA ATGGCCCGCC TGGCTGACCG
 101  CCCAACGACC CCCGCCCATT GACGTCAATA ATGACGTATG TTCCCATAGT
 151  AACGCCAATA GGGACTTTCC ATTGACGTCA ATGGGTGGAG TATTTACGGT
 201  AAACTGCCCA CTTGGCAGTA CATCAAGTGT ATCATATGCC AAGTACGCCC
 251  CCTATTGACG TCAATGACGG TAAATGGCCC GCCTGGCATT ATGCCCAGTA
 301  CATGACCTTA TGGGACTTTC CTACTTGGCA GTACATCTAC GTATTAGTCA
 351  TCGCTATTAC CATGGTGATG CGGTTTTGGC AGTACATCAA TGGGCGTGGA
 401  TAGCGGTTTG ACTCACGGGG ATTTCCAAGT CTCCACCCCA TTGACGTCAA
 451  TGGGAGTTTG TTTTGGCACC AAAATCAACG GGACTTTCCA AAATGTCGTA
 501  ACAACTCCGC CCCATTGACG CAAATGGGCG GTAGGCGTGT ACGGTGGGAG
 551  GTCTATATAA GCAGAGCTGG TTTAGTGAAC CGTCAGATCC GCTAGCGCTA
 601  CCGGACTCAG ATCTCGAGCT CAAGCTTCGA ATTCTGCAGT CGACGGTACC
 651  GCGGGCCCGG GATCCACCGG CCGGTCGCCA CCATGAGCTC CAATTCACTG
 701  GCCGTCGTTT TACAACGTCG TGACTGGGAA AACCCTGGCG TTACCCAACT
 751  TAATCGCCTT GCAGCACATC CCCCTTTCGC CAGCTGGCGT AATAGCGAAG
 801  AGGCCCGCAC CGATCGCCCT TCCCAACAGT TGCGCAGCCT GAATGGCGAA
 851  TAGGCGGCCG CGACTCTAGA TCATAATCAG CCATACCACA TTTGTAGAGG
 901  TTTTACTTGC TTTAAAAAAC CTCCCACACC TCCCCCTGAA CCTGAAACAT
 951  AAAATGAATG CAATTGTTGT TGTTAACTTG TTTATTGCAG CTTATAATGG
1001  TTACAAATAA AGCAATAGCA TCACAAATTT CACAAATAAA GCATTTTTTT
1051  CACTGCATTC TAGTTGTGGT TTGTCCAAAC TCATCAATGT ATCTTAAGGC
1101  GTAAATTGTA AGCGTTAATA TTTTGTTAAA ATTCGCGTTA AATTTTTGTT
1151  AAATCAGCTC ATTTTTTAAC CAATAGGCCG AAATCGGCAA AATCCCTTAT
1201  AAATCAAAAG AATAGACCGA GATAGGGTTG AGTGTTGTTC CAGTTTGGAA
1251  CAAGAGTCCA CTATTAAAGA ACGTGGACTC CAACGTCAAA GGGCGAAAAA
1301  CCGTCTATCA GGGCGATGGC CCACTACGTG AACCATCACC CTAATCAAGT
1351  TTTTTGGGGT CGAGGTGCCG TAAAGCACTA AATCGGAACC CTAAAGGGAG
1401  CCCCCGATTT AGAGCTTGAC GGGGAAAGCC GGCGAACGTG GCGAGAAAGG
1451  AAGGGAAGAA AGCGAAAGGA GCGGGCGCTA GGGCGCTGGC AAGTGTAGCG
1501  GTCACGCTGC GCGTAACCAC CACACCCGCC GCGCTTAATG CGCCGCTACA
1551  GGGCGCGTCA GGTGGCACTT TTCGGGGAAA TGTGCGCGGA ACCCCTATTT
1601  GTTTATTTTT CTAAATACAT TCAAATATGT ATCCGCTCAT GAGACAATAA
1651  CCCTGATAAA TGCTTCAATA ATATTGAAAA AGGAAGAGTC CTGAGGCGGA
1701  AAGAACCAGC TGTGGAATGT GTGTCAGTTA GGGTGTGGAA AGTCCCCAGG
1751  CTCCCCAGCA GGCAGAAGTA TGCAAAGCAT GCATCTCAAT TAGTCAGCAA
1801  CCAGGTGTGG AAAGTCCCCA GGCTCCCCAG CAGGCAGAAG TATGCAAAGC
1851  ATGCATCTCA ATTAGTCAGC AACCATAGTC CCGCCCCTAA CTCCGCCCAT
```

-continued

```
1901 CCCGCCCCTA ACTCCGCCCA GTTCCGCCCA TTCTCCGCCC CATGGCTGAC

1951 TAATTTTTTT TATTTATGCA GAGGCCGAGG CCGCCTCGGC CTCTGAGCTA

2001 TTCCAGAAGT AGTGAGGAGG CTTTTTTGGA GGCCTAGGCT TTTGCAAAGA

2051 TCGATCAAGA GACAGGATGA GGATCGTTTC GCATGATTGA ACAAGATGGA

2101 TTGCACGCAG GTTCTCCGGC CGCTTGGGTG GAGAGGCTAT TCGGCTATGA

2151 CTGGGCACAA CAGACAATCG GCTGCTCTGA TGCCGCCGTG TTCCGGCTGT

2201 CAGCGCAGGG GCGCCCGGTT CTTTTTGTCA AGACCGACCT GTCCGGTGCC

2251 CTGAATGAAC TGCAAGACGA GGCAGCGCGG CTATCGTGGC TGGCCACGAC

2301 GGGCGTTCCT TGCGCAGCTG TGCTCGACGT TGTCACTGAA GCGGGAAGGG

2351 ACTGGCTGCT ATTGGGCGAA GTGCCGGGGC AGGATCTCCT GTCATCTCAC

2401 CTTGCTCCTG CCGAGAAAGT ATCCATCATG GCTGATGCAA TGCGGCGGCT

2451 GCATACGCTT GATCCGGCTA CCTGCCCATT CGACCACCAA GCGAAACATC

2501 GCATCGAGCG AGCACGTACT CGGATGGAAG CCGGTCTTGT CGATCAGGAT

2551 GATCTGGACG AAGAGCATCA GGGGCTCGCG CCAGCCGAAC TGTTCGCCAG

2601 GCTCAAGGCG AGCATGCCCG ACGGCGAGGA TCTCGTCGTG ACCCATGGCG

2651 ATGCCTGCTT GCCGAATATC ATGGTGGAAA ATGGCCGCTT TTCTGGATTC

2701 ATCGACTGTG GCCGGCTGGG TGTGGCGGAC CGCTATCAGG ACATAGCGTT

2751 GGCTACCCGT GATATTGCTG AAGAGCTTGG CGGCGAATGG GCTGACCGCT

2801 TCCTCGTGCT TTACGGTATC GCCGCTCCCG ATTCGCAGCG CATCGCCTTC

2851 TATCGCCTTC TTGACGAGTT CTTCTGAGCG GGACTCTGGG GTTCGAAATG

2901 ACCGACCAAG CGACGCCCAA CCTGCCATCA CGAGATTTCG ATTCCACCGC

2951 CGCCTTCTAT GAAAGGTTGG GCTTCGGAAT CGTTTTCCGG GACGCCGGCT

3001 GGATGATCCT CCAGCGCGGG GATCTCATGC TGGAGTTCTT CGCCCACCCT

3051 AGGGGGAGGC TAACTGAAAC ACGGAAGGAG ACAATACCGG AAGGAACCCG

3101 CGCTATGACG GCAATAAAAA GACAGAATAA AACGCACGGT GTTGGGTCGT

3151 TTGTTCATAA ACGCGGGGTT CGGTCCCAGG GCTGGCACTC TGTCGATACC

3201 CCACCGAGAC CCCATTGGGG CCAATACGCC CGCGTTTCTT CCTTTTCCCC

3251 ACCCCACCCC CCAAGTTCGG GTGAAGGCCC AGGGCTCGCA GCCAACGTCG

3301 GGGCGGCAGG CCCTGCCATA GCCTCAGGTT ACTCATATAT ACTTTAGATT

3351 GATTTAAAAC TTCATTTTTA ATTTAAAAGG ATCTAGGTGA AGATCCTTTT

3401 TGATAATCTC ATGACCAAAA TCCCTTAACG TGAGTTTTCG TTCCACTGAG

3451 CGTCAGACCC CGTAGAAAAG ATCAAAGGAT CTTCTTGAGA TCCTTTTTTT

3501 CTGCGCGTAA TCTGCTGCTT GCAAACAAAA AAACCACCGC TACCAGCGGT

3551 GGTTTGTTTG CCGGATCAAG AGCTACCAAC TCTTTTTCCG AAGGTAACTG

3601 GCTTCAGCAG AGCGCAGATA CCAAATACTG TCCTTCTAGT GTAGCCGTAG

3651 TTAGGCCACC ACTTCAAGAA CTCTGTAGCA CCGCCTACAT ACCTCGCTCT

3701 GCTAATCCTG TTACCAGTGG CTGCTGCCAG TGGCGATAAG TCGTGTCTTA

3751 CCGGGTTGGA CTCAAGACGA TAGTTACCGG ATAAGGCGCA GCGGTCGGGC

3801 TGAACGGGGG GTTCGTGCAC ACAGCCCAGC TTGGAGCGAA CGACCTACAC

3851 CGAACTGAGA TACCTACAGC GTGAGCTATG AGAAAGCGCC ACGCTTCCCG

3901 AAGGGAGAAA GGCGGACAGG TATCCGGTAA GCGGCAGGGT CGGAACAGGA
```

-continued

```
3951  GAGCGCACGA GGGAGCTTCC AGGGGGAAAC GCCTGGTATC TTTATAGTCC

4001  TGTCGGGTTT CGCCACCTCT GACTTGAGCG TCGATTTTTG TGATGCTCGT

4051  CAGGGGGGCG GAGCCTATGG AAAAACGCCA GCAACGCGGC CTTTTTACGG

4101  TTCCTGGCCT TTTGCTGGCC TTTTGCTCAC ATGTTCTTTC CTGCGTTATC

4151  CCCTGATTCT GTGGATAACC GTATTACCGC CATGCAT
```

The DNA or RNA vectors may be introduced into a cell where the expression of the fusion protein can occur. The host may be a primary cell, a cell line, a unicellular microorganism, or the like, where the cell may be modified having an expression construct integrated or transiently present in the cell expressing a secretable form of EA, expressing or overexpressing a protein that the cell does not normally express under the conditions of the assay, not expressing a protein that the cell normally expresses as a result of a knockout, transcription or translation inhibitor, or the like.

The vector will include the fusion gene under the transcriptional and translational control of a promoter, usually a promoter/enhancer region, optionally a replication initiation region to be replication competent, a marker for selection, and may include additional features, such as restriction sites, PCR initiation sites, an expression construct providing constitutive or inducible expression of EA, or the like. As described above, there are numerous vectors available providing for numerous different approaches for the expression of the fusion protein in a host.

The vector may be introduced into the host cells by any convenient and efficient means, such as transfection, electroporation, lipofection, fusion, transformation, calcium precipitated DNA, etc. The manner in which the vector is introduced into the host cells will be one of efficiency and convenience in light of the nature of the host cell and the vector and the literature has numerous directions for the introduction of a vector into a host cell and the selection of the host cells that have effectively received the vector. By employing expression constructs that allow for selection, e.g. antibiotics, the cells may be grown in a selective medium, where only the cells comprising the vector will survive.

Labeling Peptides

In addition, the detection of the levels of the target could be obtained through a variety of antibody based methods such as Alpha Screen®, FRET, TR-FRET and the like. Alpha Screen® Technology is commercially available from BioTek Instruments, Inc. AlphaScreen, used mostly in high throughput screening, is a homogenous assay technology similar to TR-FRET, to some extent, which allows detection of molecular events such as binding. Coated "Donor" and "Acceptor" beads are the basis of the AlphaScreen assay technology. AlphaScreen, a bead based assay, works through the interaction of the beads coming close to each other, resulting in a cascade of chemical reactions that act to produce a greatly amplified signal. FRET and TR FRET are described, e.g. in US 2012/02191, "Detection method based on time resolved real time fluorescent energy." Other labeling peptides that could be used in place of the ED include affinity tags, such as an affinity tag, e.g. a tag derived from hemagglutinin (HA-tag; polyhistidine tag (His5-10 (SEQ ID NO: 20), preferably His6 (SEQ ID NO: 19); also referred to as His-tag), FLAG-tag), or a Myc-tag. These tags are further described, e.g. at EP2487183, "Ubiquitin-isopeptide probes."

Another possibility is horse radish peroxidsase (HRP), as described in e.g. Grigorenko et al. "A Genetically Engineered Fusion Protein with Horseradish Peroxidase as a Marker Enzyme for Use in Competitive Immunoassays," Anal. Chem. 73:1134-1139 (2001). A labeling peptide may also be a peptide having a binding epitope for an antibody, a peptide binding biotin, a peptide for attachment of FITC, etc.

Assay Applications

The assay procedure employed is to use the intact cells, either viable or non-viable. Non-viability can be achieved by heat, antibiotics, toxins, etc., which induce mortality while leaving the cells intact. The cells are grown in culture in an appropriate culture medium suitable for the cells and may be grown to confluence or subconfluence, e.g. 80%. The fusion protein expression construct and other constructs, as appropriate, may be present in the cell, integrated into the genome or may be added transiently by the various methods for introducing DNA into a cell for functional translation. These methods are amply exemplified in the literature, as previously described. By employing a marker with the protein reagent for selection of cells comprising the construct, such as antibiotic resistance, development of a detectable signal, etc., cells in culture comprising the fusion protein can be separated from cells in which the construct is absent. Once the fusion protein is being expressed, the environment of the cells may be modified, as appropriate.

Embodiments of the invention can be used in a broad range of studies for monitoring various cellular/molecular binding events. In what follows, non-limiting examples of different applications of the methods of the invention are provided. The presently disclosed systems and methods can be used to detect various interactions in a cell.

It has been shown that compounds that bind to known proteins can result in their stabilization and an increase in protein half-life intracellularly and extracellularly. E.g. a fusion protein comprising the target of interest and ED is introduced into the cell and a known compound is applied to the cells. If the compound promotes the target peptide-test compound complex formation, there will an increase in the concentration of fusion protein in cell. Lysing the cell and incubating it with EA will result in an active enzyme formation. The enzyme will act on the substrate and produce a detectable product which will indicate complex formation when compared to cells where the compound is not applied to the cells.

In certain embodiments, the methods and assays disclosed in the present application can be employed to determine the interacting interfaces through which proteins interact. The point of contacts through which proteins interacts have specific characteristics and are known as "hotspots". A fusion protein comprising target protein of different sequence lengths and ED is introduced into the cell. A particular sequence length target comprising the interacting sequences will form a complex with its interacting counterpart whereas the sequence length target which does not comprise the interacting sequence will not be able to form a complex with its interacting counterpart. As a result the fusion protein forming a complex will be stabilized whereas the fusion protein which does not form a complex will be degraded in cell. An increase in the concentration of stabilized fusion protein will be detected through complementation assay and thus will help in identifying the interacting sequences.

In certain embodiments, the methods disclosed can be used to screen small molecules that may act as inhibitors of known binding complexes. Small molecule inhibitors are an emerging choice for drug discovery studies. E.g. a fusion protein comprising a known target and ED is introduced into the cell. The target peptide interacts with the test compound and forms a complex through protein-protein interactions. Treating the cells with small molecules will result in the destabilization of fusion protein and hence will be degraded which will result in a decrease in concentration of fusion protein which will then be detected using complementation assay.

Target Peptides

A wide variety of cellular proteins having specific binding sites may be adapted for use in the present assay. The binding sites may exit in the wild type protein for binding to cell signaling molecules, natural enzymatic substrates, accessary proteins, nucleotides, polynucleotides, etc.

As one example, transcription factors are known to regulate specific gene expression patterns in response to developmental and environmental stimuli. They form specialized multi-protein complexes to regulate gene expression and thus regulating cellular responses. Thus, directly inhibiting or activating the function of a transcription factor requires specific disruption or recruitment or protein-protein or protein-DNA interactions. Therefore, the methods disclosed in the present application can be used to screen small molecules that modulate these interactions and thus will have implications in various human cancers and to develop probes for understanding the role of transcription factors in various cancers. Various transcription factors such as NFκB, JNK, STAT1, STAT2, FOXO, Sox2, SP1, RXR, RAR, Myc, Max, MAPK, HNF4, VDR among others and their interactions can be studied with the disclosed methodology.

Signaling pathways are a rich source of therapeutic targets comprised of association and dissociation of protein complexes. Signal transduction therapy has become an important area of drug research. Signaling disorders represent a major cause for various known pathological states. A number of recently identified validated target peptides of drug research are signal transduction related macromolecules. The presently disclosed methodology can be utilized to study inhibitors of known signaling complexes.

Heat shock protein –Hsp90 is one of the most abundant proteins in eukaryotic cell, comprising 1-2% of total proteins under non-stress conditions. Hsp90 interacts with and stabilizes various kinases such as ErbB2, Src, Abl, Met tyrosine kinases, cyclin dependent serine kinases among others which are key members of malignant transformation. Further, Hsp90 is also necessary for the maturation of several transcription factors, like the nuclear hormone receptors and the hypoxia-inducible factor-1. Thus, assays of Hsp90 inhibitor causing the release of the complex partner and subsequent degradation can be done using the presently disclosed methodology.

Apoptosis, or programmed cell death, is a normal component of the development and health of multicellular organisms. Cells die in response to a variety of stimuli and during apoptosis they do so in a controlled, regulated fashion. This makes apoptosis distinct from another form of cell death called necrosis in which uncontrolled cell death leads to lysis of cells, inflammatory responses and, potentially, to serious health problems. Direct initiation of apoptotic mechanisms in mammals have been suggested through TNF-induced path and the Fas induced path. Following TNF-R1 and Fas activation in mammalian cells a balance between pro-apoptotic (BAX, BID, BAK, or BAD) and anti-apoptotic (Bcl-X1 and Bcl-2) members of the Bcl-2 family is established. The presently disclosed methodology can be exploited to study various interactions leading to apoptosis.

Kinases are of great significance, such as tyrosine kinases, the MAP kinases, the cyclin dependent kinases, GTP kinases, ser/thr kinases, Chk1 and 2, etc and can be studied with the presently disclosed methodology.

Further, the methodology can be extended to neuronal proteins, such as β-amyloid, TNF, prion, APP, transporters, e.g. dopamine transporter, receptors, such as NMDA receptors, AMDA receptors, dopamine receptors, channels, etc.

In some instances, housekeeping proteins will be of interest, such as the proteins involved in the tricarboxylic acid cycle, the Krebs cycle, glycogenesis, etc.

The present methods and materials can be used to study diseases known to be caused by the degradation/destabilization of mutated proteins. For example, in lysosomal storage disorder (LSD), genetic mutations may cause a lysosomal enzyme to be misfolded [Brooks, D. A. Nat. Chem. Biol. 3, 84-85 (2007)] thus rendering it unstable and unable to move within the cell and function. [Römisch, K. Traffic. 5, 815-820 (2004).

Using the present assay, one can study the mechanism of LSD by the introduction of fusion protein (comprising the misfolded protein and labeling peptide) and then analyzing the effects of known/unknown small molecule drugs on the stabilization of fusion protein. Thus, the assay finds utility in diseases resulting from the mutated proteins like SOD1 (associated with ALS), p53 (associated with cancer). Alanine glyoxylate aminotransferase (associated with primary hyperoxaluria type 1), SMN1 (associated with spinal muscular atrophy) and can be an important tool to elucidate mechanism of action and to screening assay for small molecule drug candidates.

The present assay also finds utility in determining the half-life of mutated target peptide. Mutated peptide can be fused to a labeling peptide and a time-dependent activity can be detected in the presence and absence of binding partner to determine the half-life. Methods for measuring protein half lives can be derived using the present methods, or other, different methods known in the art. See, e.g. Yewdell et al., "Out with the old, in with the new? Comparing methods for measuring protein degradation," Cell Biol Int 35:457 (2011)

The composition, methods and assays disclosed also find utility to study proteins with tandem repeats in the sequence. Proteins with tandem repeats have a variety of binding properties and are known to be involved in protein-protein interactions and thus the studies will have great implications in elucidating the nature of known and unknown interactions, sequences involved in the interactions, compounds specific for tandem repeat structures.

Binding Sites

From the above discussion of possible target peptides, it is clear that various binding sites may be used in the present assay. Examples are (a) an ATP (nucleotide) binding site, (b) a bromodomain sequence, (c) a catalytic site or (d) an allosteric site.

The ATP-binding motif, also called the Walker motif, is a structural protein motif that is frequently found in proteins that bind ATP or GTP. It can usually be identified from just the primary structure of a protein using a fingerprint sequence that characterizes proteins as ATP or GTP-binding (see GTP-Binding Proteins). Walker et al. (1) identified two regions of sequence conservation: the A region has a stretch of small hydrophobic residues followed by [Gly/Ala]-X-X-Gly-X-Gly-Lys-Thr/Ser, where X is any residue. The second region of sequence conservation also has a stretch of small hydrophobic residues, this time ending in a conserved aspartate residue. In the three-dimensional structures of proteins having the ATP-binding motif, such as adenylate kinase, the hydrophobic residues of the A-region form a buried b-strand, and the glycine-rich region forms a loop, called the P-loop, that interacts with the phosphate of the bound nucleotide. The second conserved region codes for another hydrophobic b-strand, and the conserved aspartate is required for binding the magnesium ion that usually accompanies nucleotides bound to proteins.

As discussed above, transcription factors (including zinc finger proteins) bind to nucleotide sequences through binding sites on those molecules.

An allosteric binding site is generally defined as a site other than the protein's active site. Allosteric modulation is the regulation of proteins or enzymes by the binding of an effector molecule at the allosteric site (a site other than the proteins active site). Here, a fusion protein is constructed with a mutated peptide having an amino acid sequence other than or in addition to the active binding site (i.e. an allosteric site) and introduced into the cell. Treating the cells with various molecules who participate in binding will help in identifying the allosteric modulators of known protein as they will bind to the proteins at the non-active site and will stabilize the proteins. Allosteric sites can be drug targets, such as in the case of GPCRs. exemplified below is allosteric binding to MEKK. Allosteric JNK inhibitors are also known. Methods for identifying allosteric sites for inclusion in the present assay are described further in Patent Application WO/2003/087051, "Methods for Identifying allosteric sites".

Bromodomain sequences are described in detail in the examples below. The bromodomain (BRD), which is the conserved structural module in chromatin-associated proteins and histone acetyltranferases, is the sole protein domain known to recognize acetyl-lysine residues on proteins. These sequences are known in the literature, and, e.g described in U.S. Pat. No. 7,589,167 entitled "ZA loops of bromodomains."

The catalytic site of an enzyme, also referred to as the "active site", is the portion of the enzyme where the substrate is acted upon. For example, protein kinases are known to have a consensus pattern of about 10 amino acids in the catalytic site, as described in Prosite documentation PDOC 00100 (http (colon slash slash) prosite.expasy.org/PDOC00100). As another example, a catalytic triad refers to the three amino acid residues found inside the active site of certain protease enzymes: serine (S), aspartate (D), and histidine (H). Further descriptions of catalytic sites on enzymes may be found at http (colon slash slash)www (dot)ebi.ac.uk/thornton-srv/databases/CSA/, the EMBL catalytic site atlas.

The catalytic site of an enzyme is often found in a separate subunit. The catalytic subunits of protein kinases are highly conserved, and several structures have been solved.

Kits

Also provided by the subject invention are kits for use in practicing one or more of the above described applications. In certain embodiments, kits at least include a cell that expresses, either constitutively or inducibly, fusion protein that include a target protein and a β-galactosidase fragment, as reviewed above. In certain embodiments, kits include elements for making such cells, e.g., nucleic acids encoding fusion protein present on vectors and/or nucleic acids encoding β-galactosidase fragment to which proteins of interest can be fused using standard molecular biology techniques, as reviewed above. The kits may further include one or more additional components which find use in practicing certain embodiments of the invention, including but not limited to enzyme substrate, cell growth media, etc.

In certain embodiments, the present kits include (a) a cell comprising: a first fusion protein comprising the target protein and ED fragment of β-galactosidase, (b) EA fragment of β-galactosidase and (c) β-galactosidase substrate.

In certain embodiments, the kit may include (a) a cell comprising: a fusion protein comprising the target and ED fragment of β-galactosidase fragment; (b) EA fragment of β-galactosidase; and (c) a β-galactosidase substrate.

Also provided are kits that include (a) a cell comprising: a fusion protein comprising the target and ED fragment of β-galactosidase fragment; compound, (b) EA fragment of β-galactosidase; and (c) a β-galactosidase substrate.

Also provided are kits that include (a) a cell comprising: a fusion protein comprising the target and ED fragment of β-galactosidase fragment; small molecule, (b) EA fragment of β-galactosidase; and (c) a β-galactosidase substrate.

Also provided are kits that include (a) a cell comprising: a fusion protein comprising the variant sequence lengths of target and ED fragment of β-galactosidase fragment; (b) EA fragment of β-galactosidase; and (c) a β-galactosidase substrate.

Also provided herein are kits comprising an expression construct encoding a fusion protein comprising a target peptide fused to an ED fragment of β-galactosidase.

In certain embodiments, the vector comprises a restriction site positioned on a vector such that when a protein coding sequence is inserted into the vector using the restriction site, the vector encodes a fusion protein of the target and the β-galactosidase fragment. In certain embodiments, the kit further comprises a mammalian cell.

In addition to the above components, the subject kits may further include instructions for practicing the subject methods. These instructions may be present in the subject kit in a variety of forms, one or more of which may be present in the kit. One form in which these instructions may be present is as printed information on a suitable medium or substrate, e.g., a piece or pieces of paper on which the information is printed, in the packaging of the kit, in a package insert etc. Yet another means would be a computer readable medium, e.g., diskette, CD, etc., on which the information has been recorded. Yet another means that may be present is a website address which may be used via the internet to access the information at a removed site. Any convenient means may be present in the kits.

EXPERIMENTAL

The following examples are intended to illustrate but not limit the invention.

Example 1

Use of Binding Assay to Monitor Interaction Interfaces

Kinases bind ATP and catalyze the transfer of phosphate to target proteins. A general method of inhibiting kinase function is to apply a small molecule that blocks ATP binding to the target kinase. In this manner the compound is termed ATP-competitive.

To carry out the studies, fusions were made between the BLK and ProLabel.

The BLK (241-490)-PL amino acid sequence is shown below (SEQ ID NO. 7). The amino acid numbers 241-490 of the BLK (full length being 505 amino acids at GenBank Locus NP_001706) are shown within the sequence. The PL sequence is underlined, and the nucleotide binding sequence is bolded. The kinase domain is included in the sequence.

(SEQ ID NO. 7)
M-(241)LRLVRKLGSGQFGEVWMGYYKNNMKVAIKTLKEGTMSPEAFLGEANVMKALQHERL

VRLYAVVTKEPIYIVTEYMARGCLLDFLKTDEGSRLSLPRLIDMSAQIAEGMAYIERMNSIHRDL

RAANILVSEALCCKIADFGLARIIDSEYTAQEGAKFPIKWTAPEAIHFGVFTIKADVWSFGVLLME

VVTYGRVPYPGMSNPEVIRNLERGYRMPRPDTCPPELYRGVIAECWRSRPEERPTFEFLQSVL (490)-SSFELLES<u>SNSLAVVLQRRDWENPGVTQLNRLAAHPPFASWRNSEEARTDR</u>.

A number of fusions were constructed that included varying amounts of the protein sequence centered around the kinase active site as defined by homology to other kinases. E.g. fusion containing protein BLK amino acid numbers 241-494, 246-494, 251-494, 256-494, 261-494 and 266-494 were made.

The expression construct containing the fusion protein was used to transduce the HEK cells. The cells were then incubated in the presence of dasatinib for 3 hours.

BLK-PL fusions were then quantified by adding lysis buffer, EA and chemiluminescent substrate. It was found that a fusion with the 241-494 amino acid residues showed the highest affinity with dasatinib. Dasatinib, N-(2-chloro-6-methylphenyl)-2-[[6-[4-(2-hydroxyethyl)-1-piperazinyl]-2-methyl-4-pyrimidinyl]amino]-5-thiazole carboxamide monohydrate, is an oral multi-BCR/ABL and Src family tyrosine kinase inhibitor approved for use in patients with chronic myelogenous leukemia (CML).

Figure 3:
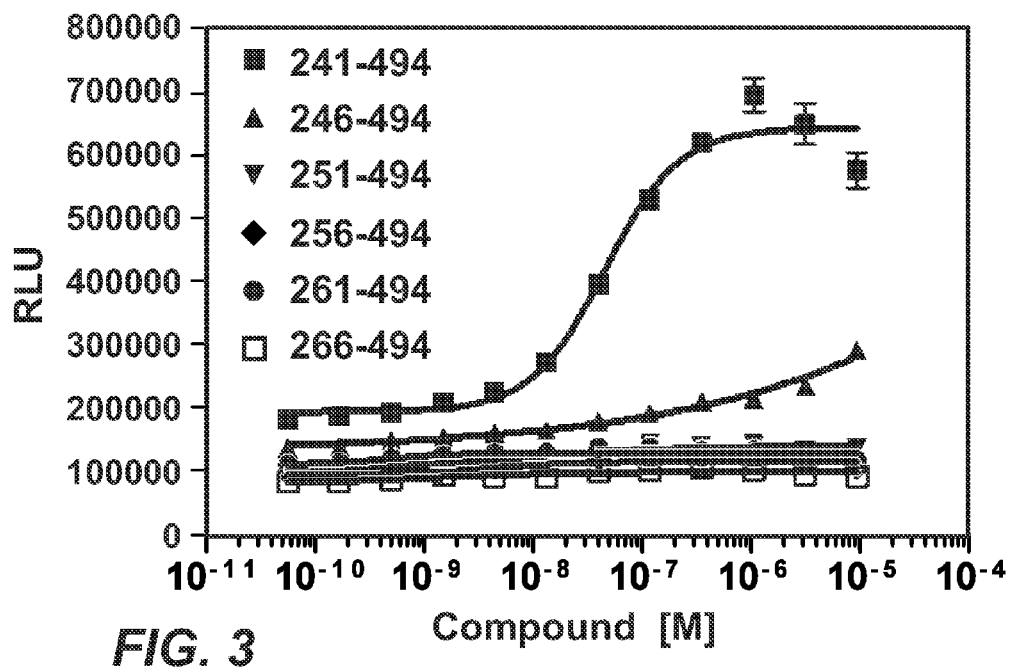
FIG. 3 is a graph showing fusion constructs (BLK-kinase-Prolabel) with varying sequence lengths of tyrosine-protein kinase BLK ("BLK") participating in interactions with a small molecule, dasatinib.

Results showing the binding of dasatinib to BLK containing amino acid sequence 241-494 are depicted in FIG. 3. The expression plasmids (e.g. 241-494) indicated in the legend are named to show the amino acid locations of the start and stop of the BLK sequence used. The plasmids were used to transduce parental U2OS cells. The cells were then treated with dasatanib for 3 hrs and the BLK-PL fusions were quantified by adding lysis buffer, EA and chemiluminescent substrate. As can be seen, the 241-494 construct showed the most robust response.

Example 2

Use of Binding Assay to Monitor Small Molecules as Inhibitors of Kinase Interactions PDL173955 is a small molecule known to complex with the C-Abl kinase domain. Foretinib (GSK1363089, XL880) is a small molecule MET and VEGFR2/KDR kinases inhibitor. Cells expressing the BLK-PL fusion were treated with the indicated ATP-competitive molecules for 6 hours. The cells were then lysed in the presence of EA and substrate; luminescence was measured 30 minutes later.

Figure 4:
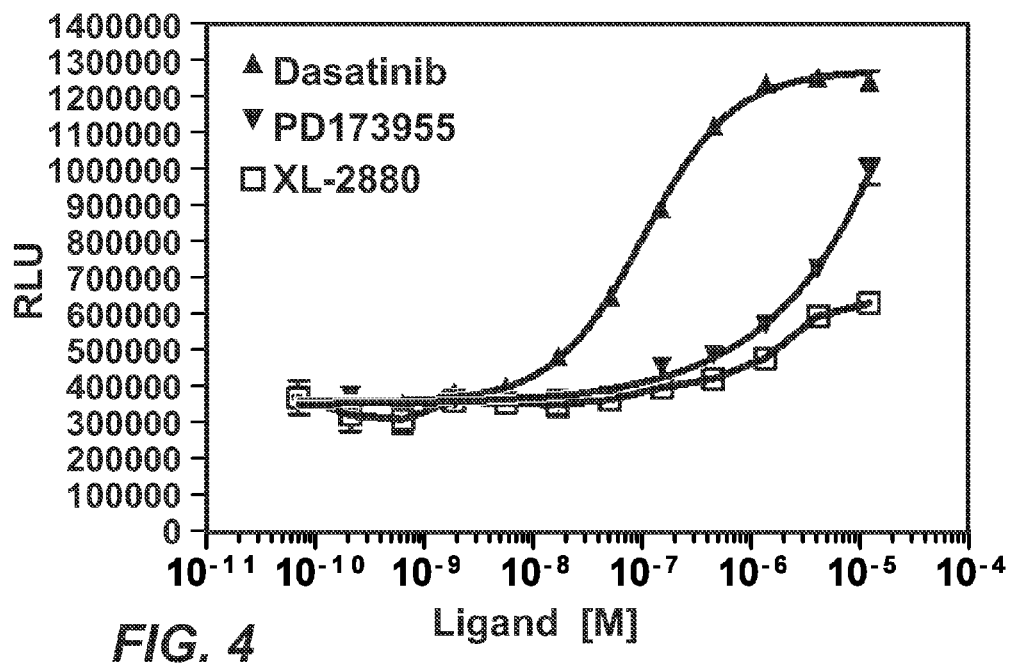
FIG. 4 is a graph showing the effect of various small molecules (dasatinib, PD173955 and XL-2880) on abundance of a BLK-PL fusion.
Figure 5:
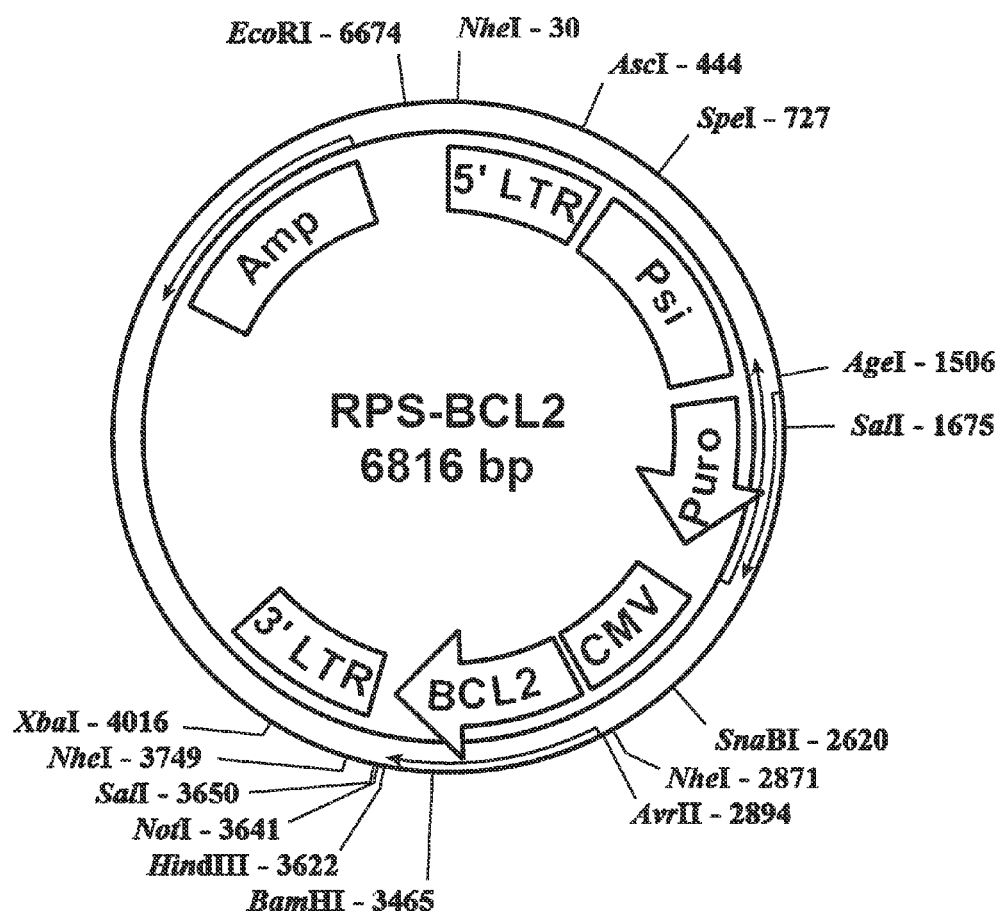
FIG. 5 is a plasmid map of an RPS-BCL2 DNA construct.
Figure 6:
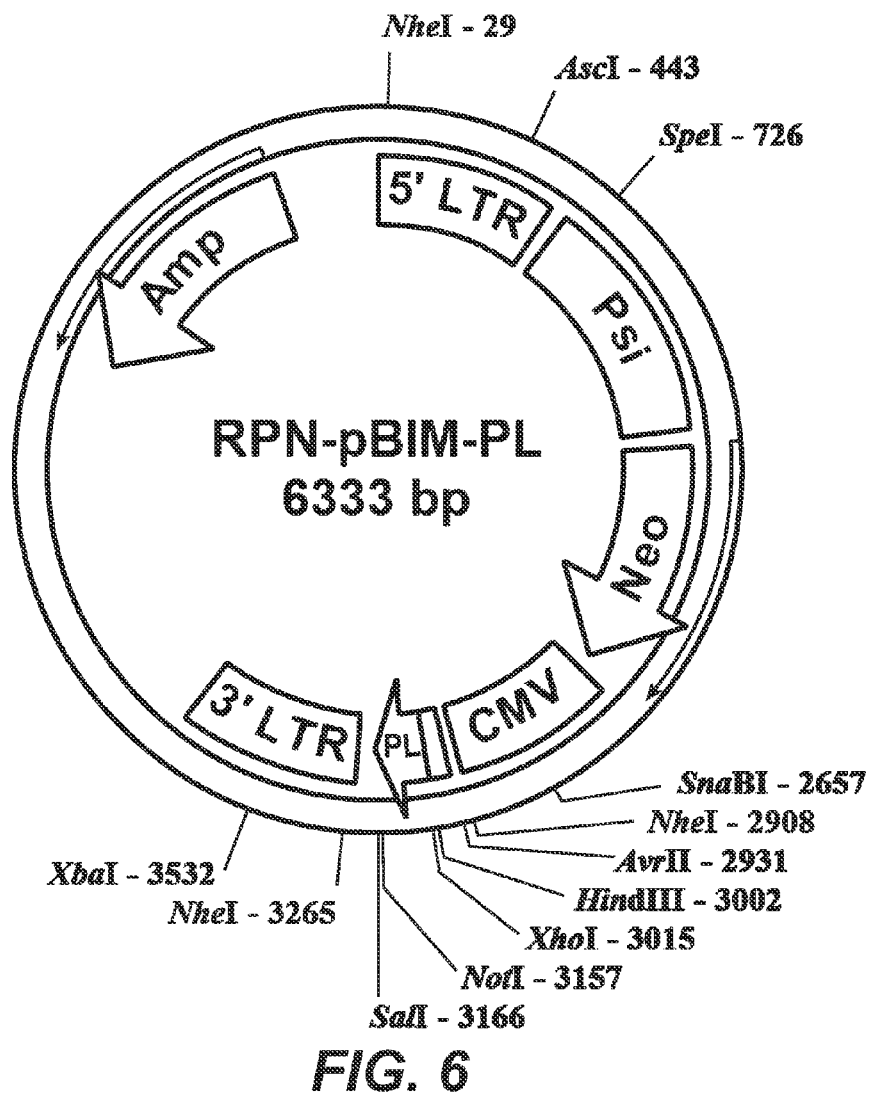
FIG. 6 is a plasmid map of an RPN-pBIM-PL DNA construct.

To carry out the binding assay to screen small molecules, fusions were made between the BLK and ProLabel, BLK-PL (SEQ ID NO. 7). The expression constructs were used to transduce HEK cells. The U2OS cell pools expressing the indicated BLK-PL fusion were shown to detect different affinity compounds (dasatinib, PD173955, XL-2880) by changes in efficacy and potency (FIG. 4).

Example 3

Use of Binding Assay to Monitor Interaction of Fusion Protein with Known Compound and Inhibition by Small Molecules B-cell lymphoma-2 (BCL2) and BCL-$X_L$ are anti-apoptotic proteins whose function is regulated by the binding of anti- or pro-apoptotic factors such as BAK (Bcl-2 homologous antagonist/killer).

As described in further detail in US 2008/0306127 entitled "Inhibiting the interaction of Bcl Proteins with binding partners," the Bcl-2 family of proteins include both anti-apoptotic molecules, such as Bcl-2 and Bcl-XL, and pro-apoptotic molecules, such as Bax, Bak, Bid and Bad. Bcl-2 contributes to cancer cell progression by preventing normal cell turnover caused by physiological cell-death mechanisms. Members of the BCL1-2 family of proteins represent key regulators of apoptosis, with pro-apoptotic (e.g., Bax, Bak, Bid, Bim, Noxa, Puma) and anti-apoptotic function (e.g., Bcl-2, Bcl-xL, Mcl-1). Selective and competitive dimerization between pro- and anti-apoptotic members of the family determines the fate of a cell given pro-apoptotic stimulus.

As is described below, truncating BCL2 will affect the stability of the protein. Various truncated BCL2 fragments can be synthesized containing varying amino acids or deletions, but containing the binding site of interest, which ordinarily will be a binding site where a small molecule, e.g. a drug candidate, will bind (see FIG. 1). For example, Bcl-2 has separate binding sites that are responsible for homodimer and heterodimer formation. See, PNAS Mar. 10, 2009 vol. 106 no. 10 3935-3940.

Interaction of BCL-2 with a peptide test compound (Bim, Bak, and Bax) was studied. Truncated peptides from Bim (SEQ ID NO. 8), Bak (SEQ ID NO. 9), and Bax (SEQ ID NO. 10) were fused to ProLabel (PL).

The amino acid sequence of the BIM fragment (SEQ ID NO. 8) (full length bim beta 5, 36 amino acids is at GenBank: AAT34900.1) is shown below:

(SEQ ID NO. 8)
MRPEIWIAQELRRIGDEFNA

The amino acid sequence of the BAK fragment (SEQ ID NO. 9) is shown below:

(SEQ ID NO. 9)
GQVGRQLAIIGDDINR full length Bak at GenBank: AAI10338.1, 153 amino acids)

The amino acid sequence of the BAX fragment (SEQ ID NO. 10) is shown below:

(SEQ ID NO. 10)
QDASTKKLSECLKRIGDELDS
(compare to full length Bax epsilon at GenBank: AAD22706.1. 164 amino acids)

The BIM-PL fusion sequence is shown below (SEQ ID NO. 11):

(SEQ ID NO. 11)
MRPEIWIAQELRRIGDEFNASSFELLESSNSLAVVLQRRDWENP

GVTQLNRLAAHPPFASWRNSEEARTDR

The native BCL-2 was co-expressed with each of the Pro-Label fusions in U2OS cells. Small molecules that are reported to disrupt BCL-2 interactions were then applied to the cells and incubated overnight.

Figure 7A:
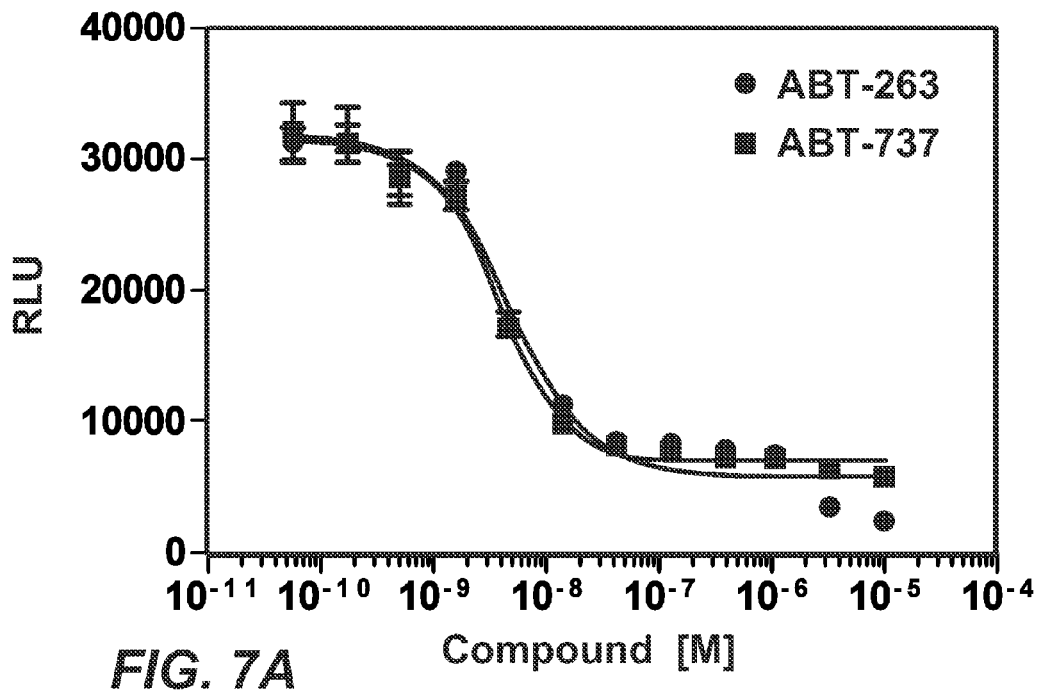
FIGS. 7A, 7B, and 7C is a series of three graphs showing the interaction of BCL-2 with fusion proteins.
Figure 7B:
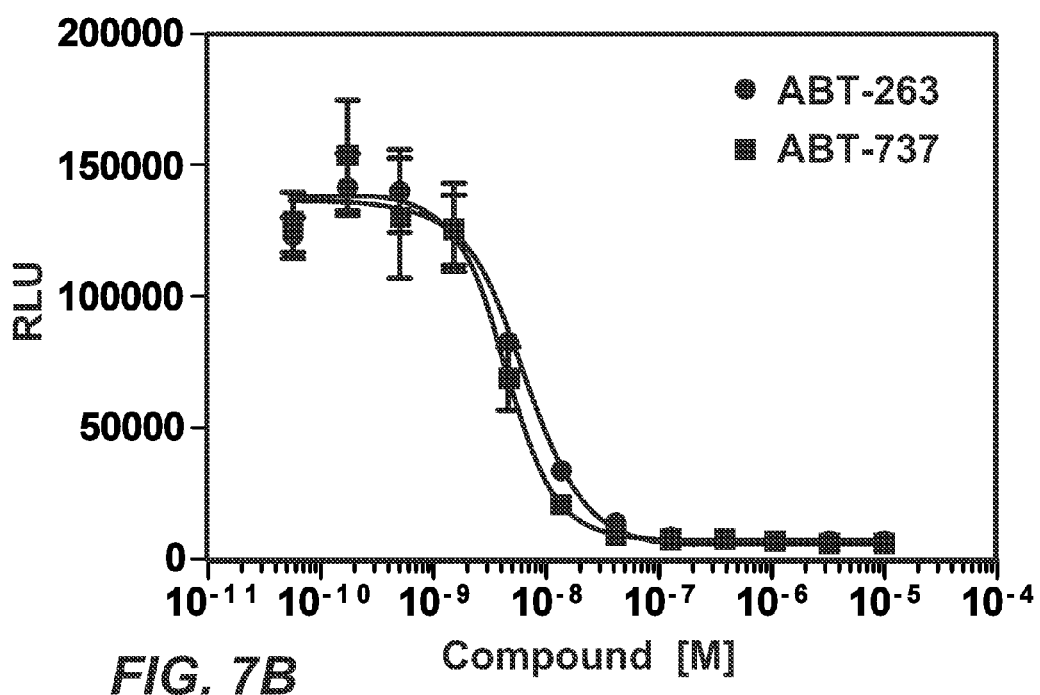
Figure 7C:
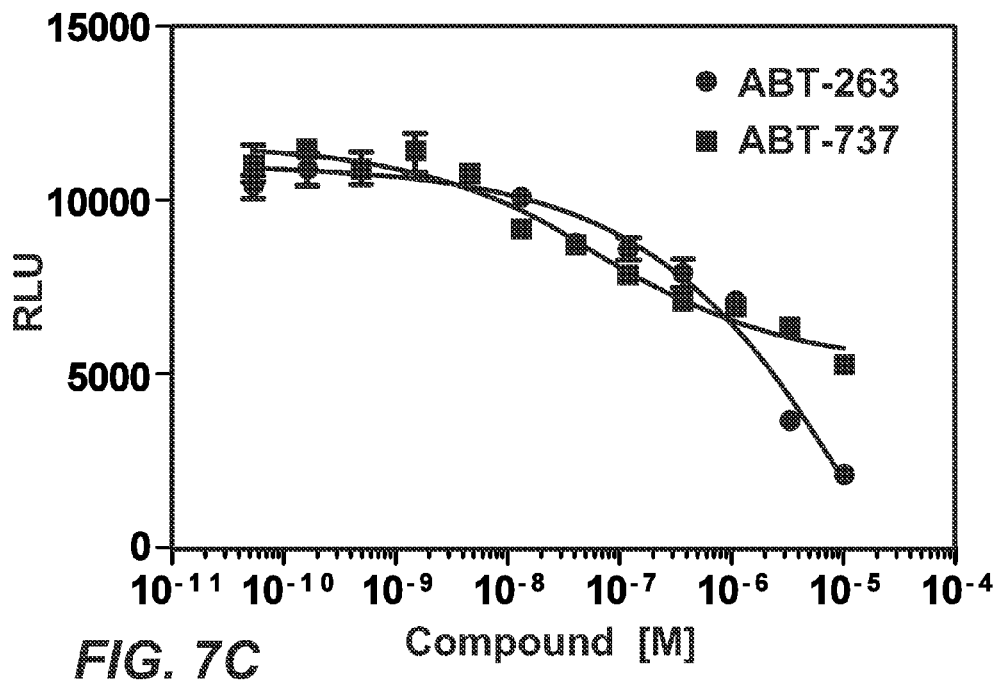

Addition of the compounds resulted in a significant loss-of-signal in all cases, but is most pronounced with the BCL-2-Bim interaction which incidentally is the highest affinity reaction (FIG. 7A-C). Cells were transduced with the indicated target PL-fusion and the untagged protein Bcl-2. The cells were treated with the indicated compounds overnight and the remaining target-PL fusion was detected by lysing the cells in the presence of EA and substrate. Luminescence was measured 30 minutes later. The following tables relate to the FIGS. 7A-C:

| 7A: Compound [M] | | |
|---|---|---|
| | ABT-263 | ABT-737 |
| Best-fit values | | |
| Bottom | 5900 | 6973 |
| Top | 31800 | 31292 |
| LogEC50 | −8.329 | −8.423 |
| HillSlope | −1.216 | −1.485 |
| EC50 | 4.683e−009 | 3.779e−009 |
| S/B = 14.0 | | 5.5 |

| 7B Compound [M] | | |
|---|---|---|
| | ABT-263 | ABT-737 |
| Best-fit values | | |
| Bottom | 6740 | 7774 |
| Top | 136900 | 139290 |
| LogEC50 | −8.221 | −8.363 |
| HillSlope | −1.635 | −1.898 |
| EC50 | 6.011e−009 | 4.335e−009 |
| S/B = 66.5 | | 26.1 |

| 7C Compound [M] | | |
|---|---|---|
| | ABT-263 | ABT-737 |
| Best-fit values | | |

| 7C Compound [M] | | |
|---|---|---|
| | ABT-263 | ABT-737 |
| Bottom | −14342 | 5446 |
| Top | 11081 | 11602 |
| LogEC50 | −4.378 | −7.191 |
| HillSlope | −0.4082 | −0.5348 |
| EC50 | 4.192e−005 | 6.437e−008 |
| S/B = 5.1 | | 2.1 |

FIG. 7B shows that addition of ABT263 (small molecule dual Bcl-2/Bcl-xL inhibitor designed to restore apoptosis) and ABT 737 (small molecule mimicking Bcl-2 antagonist BH3) prevented the stabilizing effect of Bim on BCL-2. These compounds had a somewhat similar effect on BCL-2 stabilization of Bax (FIG. 7B). These compounds had little effect on BCL-2 binding to and stabilization of Bak (FIG. 7C).

These experiments are run for a predetermined time sufficient to allow for the degradation of the PL-labeled binding peptide. This will vary with the peptide being studied, but 3 to 6 hrs. or 6 to 8 hrs was found in many cases to be optimum. Generally, a 24 hr. or less incubation period will be sufficient to observe protein stabilization according to the present methods. In cases where the binding partner (e.g. Bcl-2) and the PL-target are already bound together in the cell, sufficient time must be allowed for the small molecule to replace the peptide. The method also contemplates measuring responses at different concentrations of test compound and measurements with controls.

Example 4

Use of Binding Assay to Detect Allosteric Modulators

MEK kinases (MEKKs) comprise a family of related serine-threonine protein kinases that regulate mitogen-activated protein kinase (MAPK) signalling pathways leading to c-Jun NH2-terminal kinase (JNK) and p38 activation, induced by cellular stress (e.g., UV and gamma irradiation, osmotic stress, heat shock, protein synthesis inhibitors), inflammatory cytokines (e.g., tumor necrosis factor alpha, TNF alpha, and interleukin-1, IL1) and G protein-coupled receptor agonists (e.g., thrombin). These stress-activated kinases have been implicated in apoptosis, oncogenic transformation, and inflammatory responses in various cell types.

Interactions of kinase inhibitor small molecule compounds (U0126 and PD0325901) with the MEK-PL fusion construct were studied using the presently disclosed assay. U0126 is a highly selective inhibitor of both MEK1 and MEK2, a type of MAPK/ERK kinase. UO0126, (2Z,3Z)-2,3-bis(amino(2-aminophenylthio)methylene)succinonitrile, is known to be an allosteric inhibitor, binding outside binding outside the ATP- and ERK1/2-binding sites on MEK1/2.

PD0325901((R)—N-(2,3-dihydroxypropoxy)-3,4-difluoro-2-(2-fluoro-4-iodophenylamino)benzamide) is a selective and non ATP-competitive mitogen activated protein kinase kinase (MEK or MAPKK) MEK inhibitor.

Truncated MEK peptide containing amino acids 58-371 (see NCBI Ref SEQ NP_002746.1) was fused with the PL (SEQ ID 12). The MEK (58-371)-PL sequence is shown in (SEQ ID NO. 12). This contains the catalytic domain. The PL portion is underlined.

(SEQ ID NO. 12)
MQKVGELKDDDFEKISELGAGNGGVVFKVSHKPSGLVMARKLIHLEIKPAIRNQIIRELQ

VLHECNSPYIVGFYGAFYSDGEISICMEHMDGGSLDQVLKKAGRIPEQILGKVSIAVIKG

LTYLREKHKIMHRDVKPSNILVNSRGEIKLCDFGVSGQLIDSMANSFVGTRSYMSPERLQ

GTHYSVQSDIWSMGLSLVEMAVGRYPIPPPDAKELELMFGCQVEGDAAETPPRPRTPGRP

LSSYGMDSRPPMAIFELLDYIVNEPPPKLPSGVFSLEFQDFVNKCLIKNPAERADLKQLM

VHAFIKRSDAEEVDFSSFELLESS NSLAVVLQRRDWENPGVTQLNRLAAHPPFASWRNSE

EARTDR

The constructs were then expressed in various cell types including HEK (FIG. 8A), CHO (FIG. 8B) and U2OS (FIG. 8C) cells. Kinase inhibitors U0126 and PD0325901 were then applied to the cells.

Figure 8A:
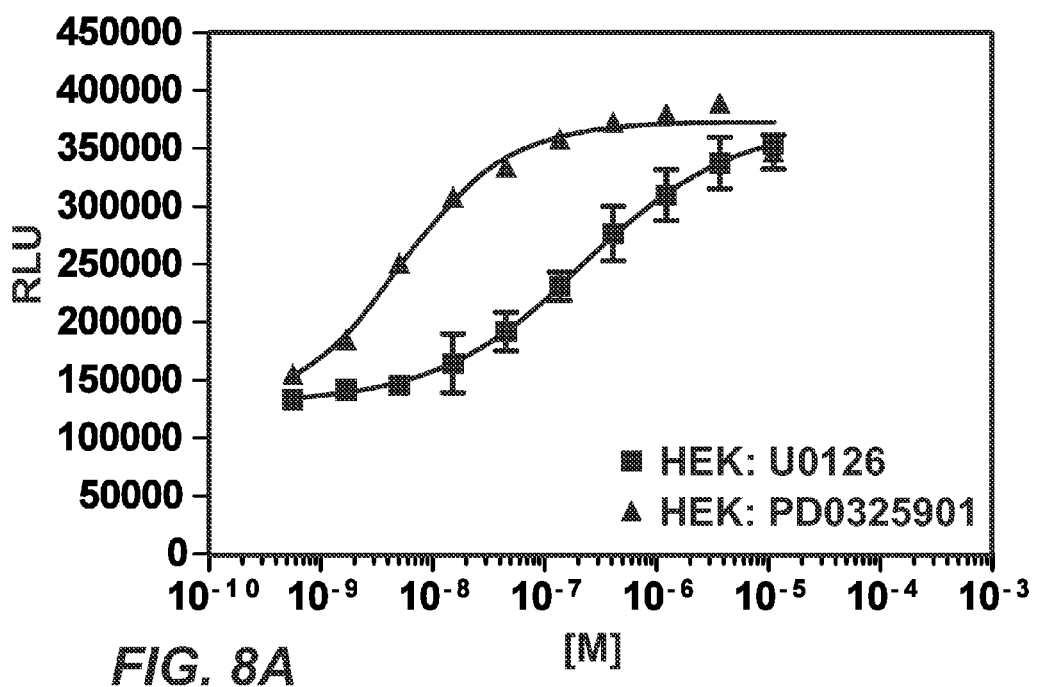
FIG. 8A is a graph showing the effect of kinase inhibitors (U0126 and PD0325901) on abundance of MEK-PL fusion interactions in HEK cells.
Figure 8B:
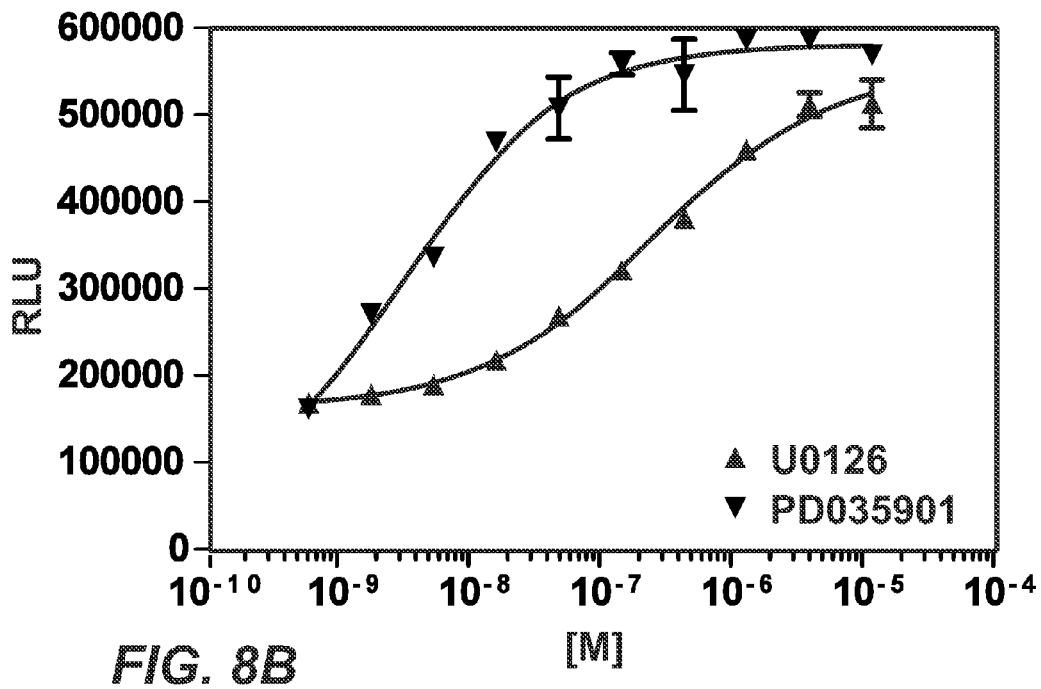
FIG. 8B is a graph as in FIG. 8A, with CHO cells.
Figure 8C:
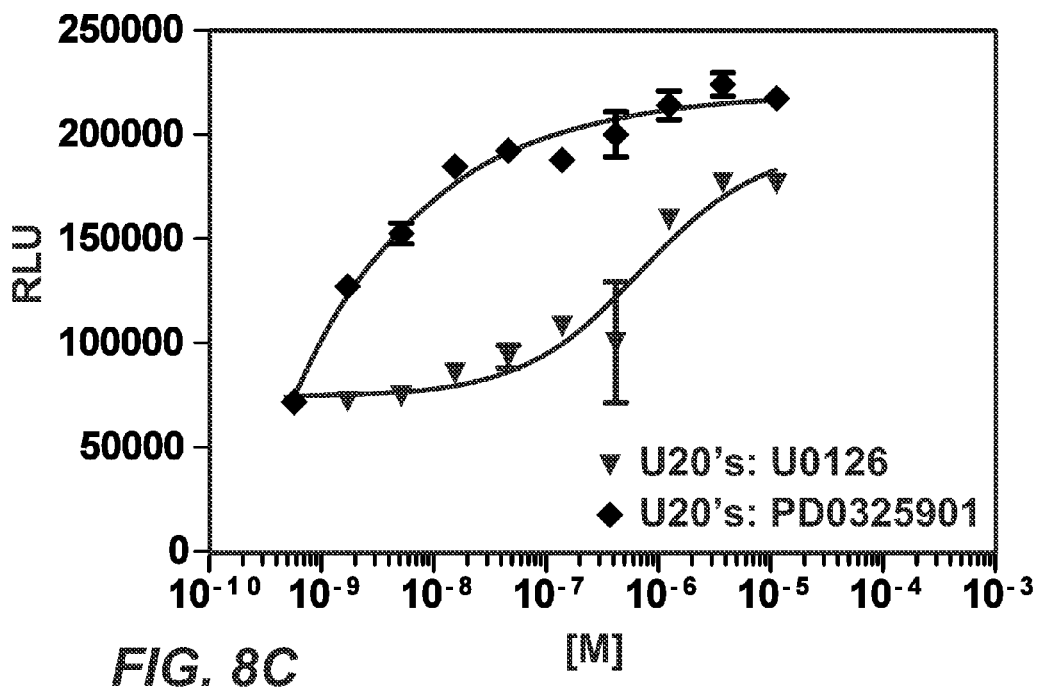
FIG. 8C is a graph as in FIG. 8A, with U2OS cells.

Binding of the compound resulted in a significant increase in the active β-galactosidase enzyme formation, giving us an indication that the compounds (known as kinase inhibitors) bound to the allosteric site rather than the active site (FIG. 8A-C).

Example 5

Use of Binding Assay to Monitor the Specificity of Binding Compounds

Dasatinib (a known ATP-competitive molecule) and U0126 and PD0325901 (known kinase inhibitors) were used to determine their specificity for ATP binding and non-ATP binding sites respectively.

Figure 9A:
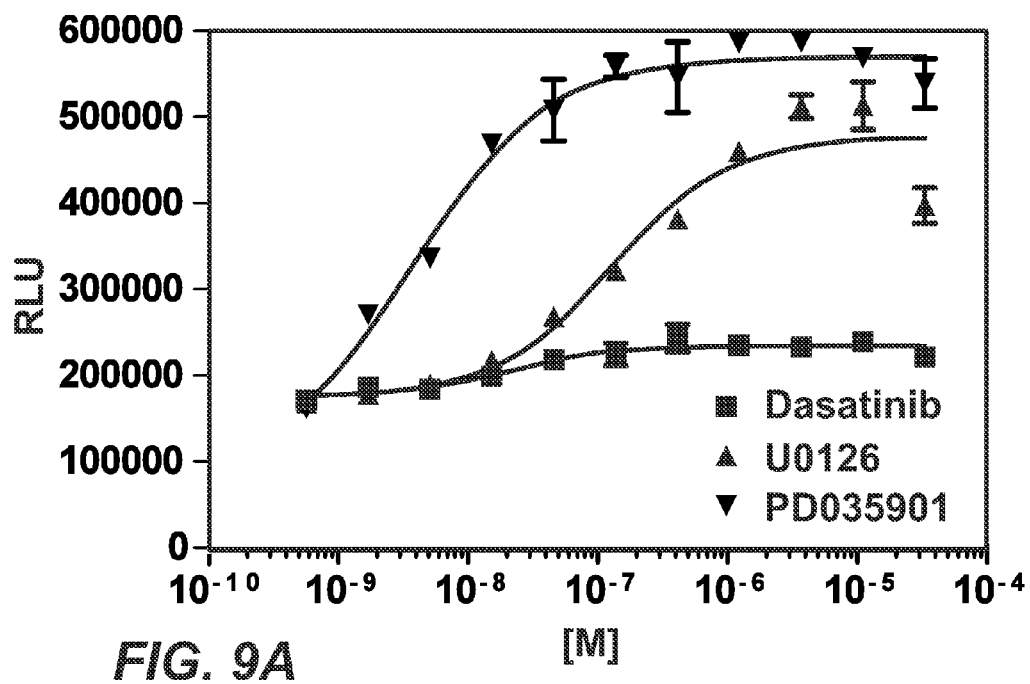
FIG. 9A is a graph showing the specificity of dasatinib, U0126 and PD035901 to MEK-PL.

Truncated MEK peptide containing amino acids from 58-371 and BLK peptide containing amino acids from 241-494 were fused with the PL. Expression construct containing MEK fusions were used to transduce CHO cells and incubated with dasatinib, U0126 and PD035901. A gain in signal was observed with U0126 and PD035901 as compared to the cells incubated with dasatinib over a period of time (FIG. 9A).

Figure 9B:
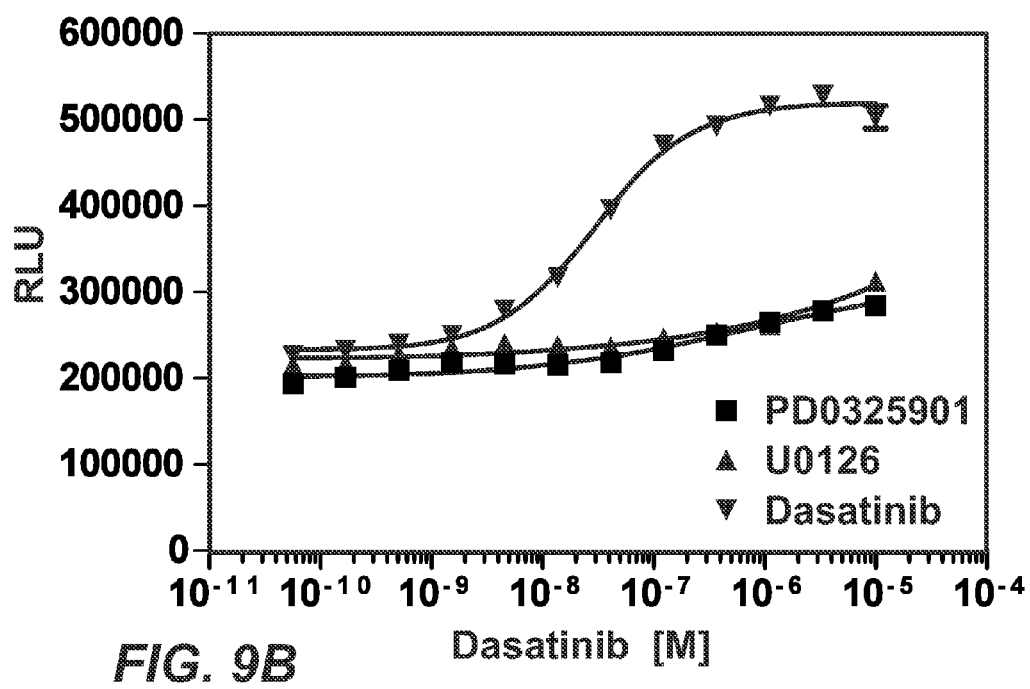
FIG. 9B is a graph as in FIG. 9A, with BLK-PL fusions.

In the second part of the experiment, expression constructs containing BLK fusions were used to transduce U2OS cells and incubated with dasatinib, U0126 and PD035901. A gain in signal was observed with dasatinib compared to the cells incubated with U0126 and PD035901 over a period of time (FIG. 9B).

As observed, dasatinib was specific for binding to the BLK fusion containing the ATP binding site and U0126 and PD035901 (kinase inhibitors) were specific for binding to the allosteric sites regulating the protein function.

Example 6

Use of Binding Assay to Study Bromodomains

Bromodomain proteins are known as epigenetic reader proteins and play an important role in the targeting of chromatin-modifying enzymes to specific sites. BRD4, for example, contains two bromodomains, a conserved sequence motif which may be involved in chromatin targeting.

To study the effect of compound binding, fusion proteins were prepared using fragments of BRD4 (1) (Accession No. NM_058243), BRD2 (1) (Accession No. NM_005104) and BRDT (1) (Accession No. NM_001242806) (SEQ ID NO. 13, 14 and 15 respectively) and prolabel (PL). The expression construct containing the fusion proteins were used to transducer the HEK cells. Cells were plated in a 384 well-plate and incubated overnight at 37° C./5% CO2 to allow the cells to attach and gro. These sequences are listed as follows:

```
BRD4(1) (SEQ ID NO. 13), ED portion underlined for clarity
MKVSEQLKCCSGILKEMFAKKHAAYAWPFYKPVDVEALGLHDYCDIIKHPMDMSTIKS

KLEAREYRDAQEFGADVRLMFSNCYKYNPPDHEVVAMARKLQDVFEMRFAKMPSSFE

LLESS NSLAVVLQRRDWENPGVTQLNRLAAHPPFASWRNSEEARTDR

BRD2(1) (SEQ ID NO. 14) ED portion underlined for clarity
MRVTNQLQYLHKVVMKALWKHQFAWPFRQPVDAVKLGLPDYHKIIKQPMDMGTIKR

RLENNYYWAASECMQDFNTMFTNCYIYNKPTDDIVLMAQTLEKIFLQKVASMPQEEQE

LVSSFELLESSNSLAVVLQRRDWENPGVTQLNRLAAHPPFASWRNSEEARTDR

BRDT(1) (SEQ ID NO. 15) ED portion underlined for clarity
MLTNQLQYLQKVVLKDLWKHSFSWPFQRPVDAVKLQLPDYYTIIKNPMDLNTIKKRLE

NKYYAKASECIEDFNTMFSNCYLYNKPGDDIVLMAQALEKLFMQKLSSFELLESSNSLA

VVLQRRDWENPGVTQLNRLAAHPPFASWRNSEEARTDR
```

The cells were then exposed to a control compound (JQ1) and incubated for 6 hrs at 37° C. the fusion proteins were then quantified by adding lysis buffer, EA and detection substrate and an increase in stability of fusion protein was observed following compound binding.

Further, the assay can also be applied to proteins which consist of bromodomains as tandem domains (BRD-BRD, PHD-BRD or BRD-PHD) which are tightly associated with each other in sequence. To carry out the binding assays-fusions were prepared between BRDT (tandem) and BRD (3) (tandem, SEQ ID NO. 16) with –PL.

BRD3(1-403)-PL                                    (SEQ ID NO. 16)
MSTATTVAPAGIPATPGPVNPPPPEVSNPSKPGRKTNQLQYMQNVVVKTLWKHQFAWP

FYQPVDAIKLNLPDYHKIIKNPMDMGTIKKRLENNYYWSASECMQDFNTMFTNCYIYN

KPTDDIVLMAQALEKIFLQKVAQMPQEEVELLPPAPKGKGRKPAAGAQSAGTQQVAAV

SSVSPATPFQSVPPTVSQTPVIAATPVPTITANVTSVPVPPAAAPPPATPIVPVVPPTPPVV

KKKGVKRKADTTTPTTSAITASRSESPPPLSDPKQAKVVARRESGGRPIKPPKKDLEDGE

VPQHAGKKGKLSEHLRYCDSILREMLSKKHAAYAWPFYKPVDAEALELHDYHDIIKHP

MDLSTVKRKMDGREYPDAQGFAADVRLMFSNCYKYNPPDHEVVAMARKSNCCISFEL

LESSNSLAVVLQRRDWENPGVTQLNRLAAHPPFASWRNSEEARTDR

Following the above mentioned experimental conditions and control compound (JQ1) fusion proteins were quantified for the stability and an increase in the half-life (stability) was observed in tandem repeat domains following compound binding.

Example 7

Use of Binding Assay to Study the Effect of Compound Binding on Half-Life of a Transferase Enzyme in a Cell Methyltransferases are a group of transferases enzymes involved in DNA methylation. G9a methyltransferase methylates lysine 9 of histone H3 and is present in humans. For the present assay, the catalytic domain of G9A methyltransferase (a.a. 918-1193, accession no. NM_006709) was fused at its C-terminus to PL tag (detection peptide, underlined below) (SEQ ID NO. 17).

```
G9A(918-1198)-PL (SEQ ID NO. 17), PL underlined for clarity
MTEKIICRDVARGYENVPIPCVNGVDGEPCPEDYKYISENCETSTMNIDRNITHLQHCTCVDDCSS

SNCLCGQLSIRCWYDKDGRLLQEFNKIEPPLIFECNQACSCWRNCKNRVVQSGIKVRLQLYRTA

KMGWGVRALQTIPQGTFICEYVGELISDAEADVREDDSYLFDLDNKDGEVYCIDARYYGNISRFI

NHLCDPNIIPVRVFMLHQDLRFPRIAFFSSRDIRTGEELGFDYGDRFWDIKSKYFTCQCGSEKCKH

SAEAIALEQSRLARLDLSFELLESSNSLAVVLQRRDWENPGVTQLNRLAAHPPFASWRNSEEART

DR
```

Figure 10:
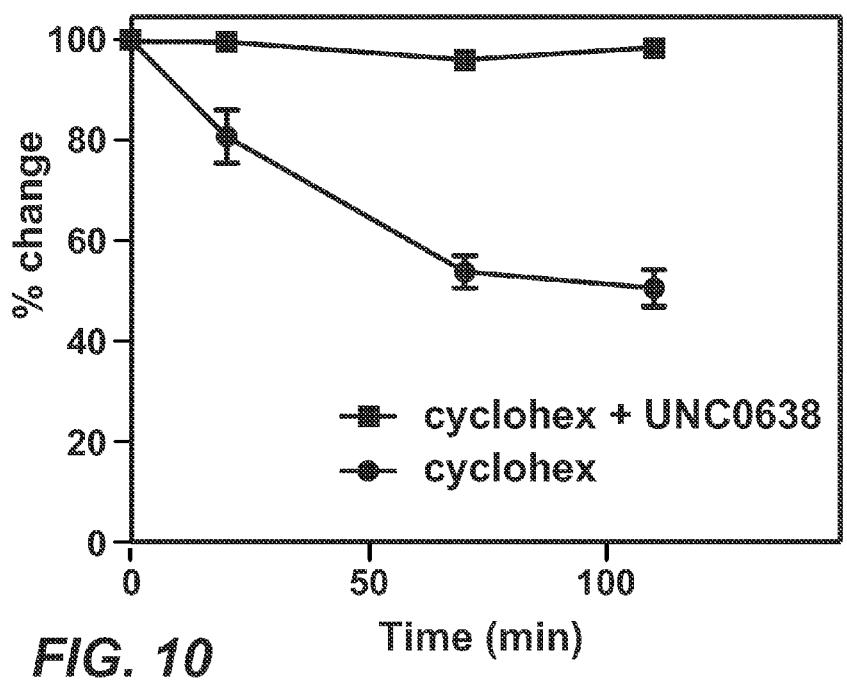
FIG. 10 is a graph showing change in luminescence in a histone methylase G9a fragment when treated with UNC0638, a selective chemical probe for G9a/GLP methyltransferases.

The enzyme donor PL fused to the catalytic domain of G9A was expressed in A549 cells, which were plated I a 384-well plate and incubated overnight at 37° C./5% CO2 to allow the cells to attach and grow. Cells expressing fusion protein were divided into 2 batches, one serving as control and other treated with binding compound (UNC0638) for 6 hrs at 37° C. Both the batches were then treated with cycloheximide to prevent further protein production and the half-life of the fusion protein in both the batches were calculated as shown in FIG. 10. As can be seen, after 100 minutes the percent change in luminescence of the UNC0638 treated cells was minimal, while the cells treated with only cycloheximide had dropped approximately 50%. UNC0638 is commercially available and is an inhibitor of G9a/GLP methyltransferases. See, e.g. http (colon slash slash) apps.thesgc.org/chemical_probes/UNC0638/#overview, SGC product literature.

As also can be seen from the graph in FIG. 10, the half-life of fusion-protein with binding partner (UNC 0638) is greater as compared to fusion protein not exposed to the binding partner, indicating that the truncated fragment having amino acids 918-1198 was destabilized.

Example 8

Use of Binding Assay to Study Cytochrome $P_{450}$

Cytochrome P450 (CYPs) are a major class of enzymes participating in drug metabolism and thus also act as a marker in drug designing/discovery studies.

Figure 11:
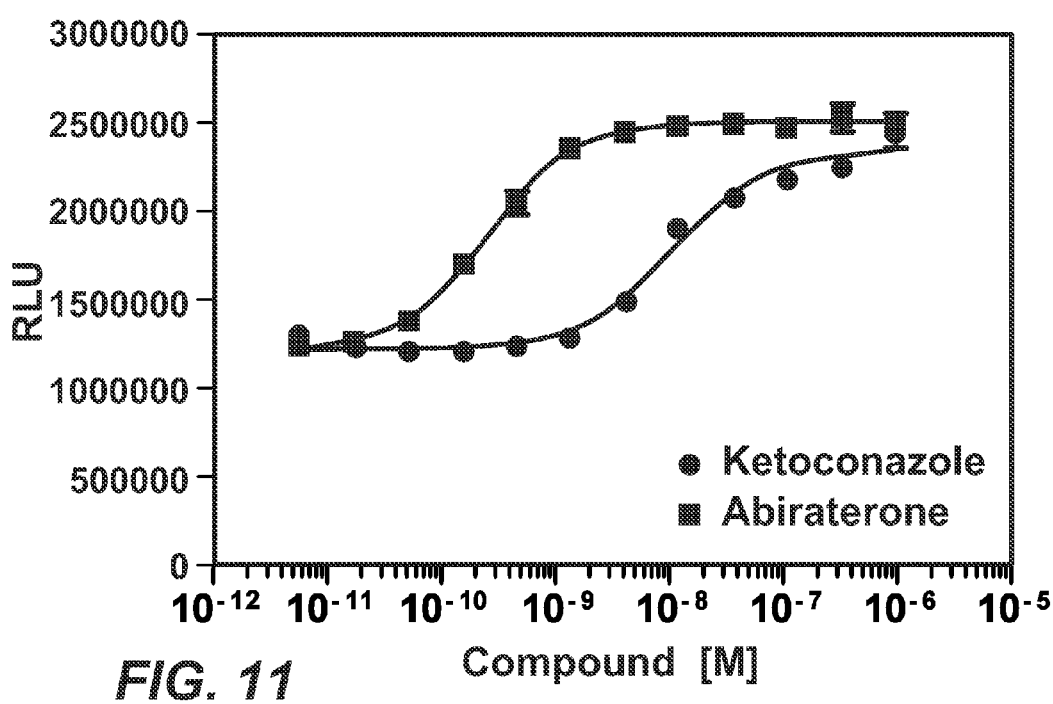
FIG. 11 is a graph showing fluorescence from a CYP 17 A-ED fusion, shows stabilization of that domain with Ketoconazole and Abiraterone.

Catalytic domain of each CYP (CYP19A accession no. NM_000103; SEQ ID NO. 18 and CYP 17A, accession no. NM_000102; SEQ ID NO. 19) was fused at its C-terminus to the PL tag. HEK cells were transduced with fusion protein expression construct. The cells were then treated with different compounds for 3-6 hrs at 37° C. the fusion proteins were then quantified to analyze the effect of different compounds on the stabilization of fusion proteins. The following best-fit values were obtained, and the data for CYP 17 A is shown in FIG. 11, which shows stabilization of that domain with Ketoconazole and Abiraterone, with the following best fit data:

|  | Ketoconazole | Abiraterone |
|---|---|---|
| Best-fit values |  |  |
| Bottom | 1.230e+006 | 1.231e+006 |
| Top | 2.348e+006 | 2.516e+006 |
| LogEC50 | −7.988 | −9.598 |
| HillSlope | 1083 | 1.152 |
| EC50 | 1.028e−008 | 2.522e−010 |
| S/B = 1.9 |  | 2.0 |

CYP17 localizes to the endoplasmic reticulum. It has both 17alpha-hydroxylase and 17,20-lyase activities and is a key enzyme in the steroidogenic pathway that produces progestins, mineralocorticoids, glucocorticoids, androgens, and estrogens. Ketoconazole is an imidazole medicine used to treat fungal infections. It binds to the fungal p450 enzymes, and is shown here to bind to CYP17a. Abiratone, CAS 154229-19-3, is known to be a potent CYP17 inhibitor Using CYP 19A amino acids 1-503, it was also found that anastrazole and YM511 stabilized that fusion peptide (data not shown). Arimidex® anastrazole is available from Astra-Zeneca and is known to bind to aromatase. YM511 (chemical Name: 4-[[(4-Bromophenyl)methyl]-4H-1,2,4-triazol-4-ylamino]benzonitrile) is also an aromatase inhibitor. CYP19 is also known as aromatase.

```
CYP17A (SEQ ID NO. 18), with ED underlined for clarity:
MWELVALLLLTLAYLFWPKRRCPGAKYPKSLLSLPLVGSLPFLPRHGHMHNNEEKLQKKYGPIYSVRMGT

KTTVIVGHHQLAKEVLIKKGKDFSGRPQMATLDIASNNRKGIAFADSGAHWQLHRRLAMATFALFKDGDQ

KLEKIICQEISTLCDMLATHNGQSIDISFPVFVAVTNVISLICFNTSYKNGDPELNVIQNYNEGIIDNLSKDSLV

DLVPWLKIFPNKTLEKLKSHVKIRNDLLNKILENYKEKFRSDSITNMLDTLMQAKMNSDNGNAGPDQDSEL

LSDNHILTTIGDIFGAGVETTTSVVKWTLAFLLHNPQVKKKLYEEIDQNVGFSRTPTISDRNRLLLLEATIRE

VLRLRPVAPMLIPHKANVDSSIGEFAVDKGTEVIINLWALHHNEKEWHQPDQFMPERFLNPAGTQLISPSVS

YLPFGAGPRSCIGEILARQELFLIMAWLLQRFDLEVPDDGQLPSLEGIPKVVFLIDSFKVKIKVRQAWREAQ

AEGSTSSELLLESSNSLAVVLQRRDWENPGVTQLNRLAAHPPFASWRNSEEARTDR
```

CONCLUSION

The above specific description is meant to exemplify and illustrate the invention and should not be seen as limiting the scope of the invention, which is defined by the literal and equivalent scope of the appended claims. All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from actual publication dates which may need to be independently confirmed.

What is claimed is:

1. A method to assess binding of a compound to a binding site of a target peptide in a cell, comprising:

(a) providing in the cell a fusion protein comprising (i) a target peptide having a destabilizing mutation and (ii) a labeling peptide;

(b) incubating a mixture of the cell of (a) and the compound for a period sufficient to allow binding of the compound to the binding site of the target peptide and to allow for stabilization of the fusion protein by the binding, then (c) combining the mixture from step (b) with a label that detects an amount of the labeling peptide remaining after incubating, wherein a change in the amount of labeling peptide detected indicates binding of the compound to the target peptide.

2. The method of claim 1 wherein the compound is one of a small molecule, a peptide, and a full-length protein.

3. The method of claim 1 wherein the compound inhibits binding of the target peptide to a native ligand for the target peptide.

4. The method of claim 1 wherein the binding site is one of (a) an ATP binding site, (b) a bromodomain sequence, (c) a catalytic site or (d) an allosteric site.

5. The method of claim 1 wherein the labeling peptide is selected from the group consisting of (a) an enzyme donor fragment of β-galactosidase, and (b) a peptide having a binding epitope for a secondary label.

6. The method of claim 5 wherein the labeling peptide is an enzyme donor ("ED") having a sequence according to one of SEQ ID NO: 1, SEQ ID NO: 2, SEQ ID NO: 3, or SEQ ID NO: 4.

7. The method of claim 6 wherein the labeling peptide is detected by an enzyme acceptor ("EA") that has a sequence according to SEQ ID NO: 5.

8. The method of claim 1 wherein the cell is a mammalian cell.

9. The method of claim 1 further comprising the step of carrying out steps (a) through (c) in the absence of the compound to provide a control for determining the change in the amount of labeling peptide detected.

10. The method of claim 1 wherein said target peptide comprises a mutation which is a truncation, said mutation being outside of the binding site.

11. The method of claim 1 wherein said target peptide comprises a mutation which is a deletion of at least ten percent of the sequence of the full length protein.

12. A method to assess a compound as binding to a binding site on target peptide in a cell, comprising:
   (a) providing cells expressing a fusion protein comprising (i) said target peptide, having therein a destabilizing mutation, and (ii) a labeling peptide;
   (b) incubating a first number of cells from step (a) with said compound and a second number of cells from step (a) without said compound for a period sufficient to allow binding of the compound to the binding site of the target peptide and to allow for stabilization of the fusion protein by the binding of the compound, then
   (c) adding to samples incubated in step (b) a label that detects an amount of the labeling peptide remaining in the cell after said incubating, whereby a difference in the amount of labeling peptide between the first number of cells and the second number of cells indicates binding of the compound to the target peptide.

13. The method of claim 12 wherein said compound is one of a small molecule, a peptide, and a full-length protein.

14. The method of claim 12 further comprising the step of adding a second compound that competes for binding with the compound of step (b).

15. The method of claim 12 wherein said binding site is one of (a) an ATP binding site, (b) a bromodomain sequence, (c) a catalytic site or (d) an allosteric site.

16. The method of claim 12 wherein said labeling peptide is (a) an ED or (b) a binding epitope for a labeling peptide.

17. The method of claim 16 wherein said labeling peptide is an ED having a sequence according to one of SEQ ID NO: 1, SEQ ID NO: 2, SEQ ID NO: 3, or SEQ ID NO: 4.

18. The method of claim 12 wherein said cell is a mammalian cell.

19. The method of claim 12 wherein said target peptide comprises a mutation which is a truncation, said mutation being outside of the binding site.

20. The method of claim 12 wherein said target peptide comprises a mutation which is a deletion, said mutation being outside of the binding site.

21. The method of claim 14 wherein said second compound is one of a small molecule, a peptide, and a full-length protein.

* * * * *